United States Patent [19]
Yoshinaga et al.

[11] Patent Number: 5,973,042
[45] Date of Patent: *Oct. 26, 1999

[54] HIGHLY WATER-ABSORPTIVE POLYMERS HAVING ENHANCED GEL STRENGTH

[75] Inventors: Kenji Yoshinaga; Shozo Kitagawa; Toshiko Nakamura; Miho Tanaka; Kiichi Ito, all of Yokkaichi, Japan

[73] Assignee: Mitsubishi Chemical Corporation, Tokyo-To, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/664,311

[22] Filed: Jun. 11, 1996

Related U.S. Application Data

[63] Continuation of application No. 08/231,047, Apr. 22, 1994, abandoned.

[30] Foreign Application Priority Data

| Apr. 23, 1993 | [JP] | Japan | 5-120678 |
| Aug. 30, 1993 | [JP] | Japan | 5-213928 |
| Oct. 15, 1993 | [JP] | Japan | 5-289699 |
| Nov. 11, 1993 | [JP] | Japan | 5-282708 |
| Feb. 16, 1994 | [JP] | Japan | 6-019677 |

[51] Int. Cl.$^6$ .................. C08K 5/20; C08K 5/11; C08K 5/098; C08K 5/057; C08K 3/30; C08K 3/22; C08K 5/25

[52] U.S. Cl. .................... 524/192; 524/209; 524/227; 524/228; 524/306; 524/314; 524/321; 524/398; 524/780; 524/783; 524/831; 524/832; 524/847

[58] Field of Search ................... 524/229, 398, 524/399, 400, 397, 321, 306, 205, 209, 192, 413, 382, 832, 831, 847, 783, 780, 227, 228, 314, 777, 823, 819, 916, 497; 523/207, 209, 333, 334; 424/78.26, 78.34; 514/772.6

[56] References Cited

U.S. PATENT DOCUMENTS

| 3,178,389 | 4/1965 | Hallenbeck ............ 524/916 |
| 3,402,137 | 9/1968 | Fischer et al. . |
| 3,660,134 | 5/1972 | Morris et al. . |
| 3,781,948 | 1/1974 | Caldwell . |
| 3,790,514 | 2/1974 | Economon . |
| 3,867,329 | 2/1975 | Halpern et al. . |
| 3,948,841 | 4/1976 | Dusek . |
| 4,025,483 | 5/1977 | Ramig . |
| 4,043,952 | 8/1977 | Ganslaw et al. . |
| 4,090,013 | 5/1978 | Ganslaw et al. . |
| 4,137,182 | 1/1979 | Golinkin . |
| 4,250,070 | 2/1981 | Ley et al. . |
| 4,283,387 | 8/1981 | Young et al. . |
| 4,286,082 | 8/1981 | Tsubakimoto et al. . |
| 4,397,984 | 8/1983 | Wendel et al. . |
| 4,407,991 | 10/1983 | Messick . |
| 4,525,527 | 6/1985 | Takeda et al. . |
| 4,539,348 | 9/1985 | Gajria . |
| 4,552,938 | 11/1985 | Makita et al. . |
| 4,587,308 | 5/1986 | Makita et al. . |
| 4,753,829 | 6/1988 | Panush . |
| 4,863,989 | 9/1989 | Obayashi et al. . |
| 4,917,186 | 4/1990 | Mumallah . |
| 4,954,562 | 9/1990 | Anderson . |
| 5,013,769 | 5/1991 | Murray et al. . |
| 5,082,056 | 1/1992 | Tackett . |
| 5,096,944 | 3/1992 | Itou et al. ............ 524/916 |
| 5,262,458 | 11/1993 | Bastioli et al. . |
| 5,412,019 | 5/1995 | Roulstone et al. ............ 524/413 |
| 5,519,088 | 5/1996 | Itoh et al. ............ 524/413 |

FOREIGN PATENT DOCUMENTS

| 2559158 | 8/1985 | France . |
| 63-105064 | 5/1988 | Japan . |
| 521355 | 1/1993 | Japan . |

*Primary Examiner*—Veronica P. Hoke
*Attorney, Agent, or Firm*—Armstrong, Westerman, Hattori, McLeland & Naughton

[57] ABSTRACT

There is provided a highly water-absorptive polymer composition comprising:
(A) 100 parts by weight of a highly water-absorptive polymer having a crosslinked structure, comprising as its constituent a carboxyl group and/or a carboxylate group; and
(B) 0.05 to 10 parts by weight of an additive selected from the group consisting of an oxalic acid (salt) compound, a sulfate of a metal selected from titanium, zirconium and vanadium, and a crystalline or noncrystalline, high-purity particulate titania having a mean particle diameter of 1 μm or less, a specific surface area of 10 m$^2$/g or more as determined by the Brunauer-Emmett-Teller method, and, when crystalline, a crystal structure of a mixed type of rutile and anatase.

There is also provided a method for producing a highly water-absorptive polymer having enhanced gel strength, which comprises treating with an alkoxytitanium a highly water-absorptive polymer having a crosslinked structure, comprising as its constituent a carboxyl group and/or a carboxylate group.

19 Claims, 2 Drawing Sheets

HIGHLY WATER-ABSORPTIVE POLYMERS HAVING ENHANCED GEL STRENGTH

This application is a continuation of application Ser. No. 08/231,047 filed Apr. 22, 1994, now abandoned.

BACKGROUND OF THE INVENTION

1. Field of the Invention

This invention relates to highly water-absorptive polymers having enhanced gel strength. More particularly, this invention relates to highly water-absorptive polymer compositions exhibiting enhanced strength and stability of a gel impregnated with water, especially with a body fluid such as urine, and a method for producing highly water-absorptive polymers having such excellent gel properties.

2. Background Art

In recent years, highly water-absorptive polymers have been practically used not only in the field of sanitary goods such as sanitary napkins and disposable paper diapers but also for a variety of industrial materials such as water-retaining materials, dew condensation-preventing materials freshness-preserving materials and solvent-dehydrating materials. They have been put to practical use also in the fields of afforestation, agriculture and horticulture. Thus, their application is now becoming wider.

Of these application fields, sanitary goods such as sanitary napkins, disposable paper diapers and pads for those who are suffering from incontinence have been improved in a feeling upon use due to improvements in the materials used, various types of gathers, and the like. Therefore, the time during which the sanitary goods can be comfortably used is becoming longer. Also, a case where the highly water-absorptive polymers are used under extremely severe conditions is now being increased in the fields of industrial materials, agriculture and horticulture.

A highly water-absorptive polymer takes the form of a gel when it absorbs body fluids such as urine, menstrual blood and sweat. Such a gel deteriorates and decomposes with time and loses its strength, and, at the same time, the surface and inner part of the gel become sticky. Namely, the liquid-retaining properties of the gel become worse with time. Such problems caused by this that a liquid runs out without being absorbed in a sanitary good upon use, and that a feeling upon use of a sanitary good becomes worse with time, are becoming more serious as the time during which a sanitary good is used is now becoming longer.

Reasons for the deterioration and decomposition of the gel are not fully clarified so far. It is however assumed that an extremely small amount of active impurities contained in body fluids such as urine accelerate the decomposition of a highly water-absorptive polymer gel in accordance with a single mechanism or a plurality of mechanisms. The degree of and the behavior in the decomposition of the polymer gel vary widely depending upon the state of the gel when a liquid is absorbed therein and individuals' differences in a body fluid.

Under these circumstances, there has been demanded a highly water-absorptive polymer having gel properties of excellent strength and stability with time, which is always stable to body fluids such as urine regardless of individuals' differences.

As a method for improving the strength and stability of a gel, it may be considered to increase the crosslinking density of a highly water-absorptive polymer. This method, however, entails a problem of decrease in the water absorption capacity of the polymer.

Japanese Patent Kokai Publication No. 63-118375 proposes a method in which an oxygen-containing reducing inorganic salt and/or an organic antioxidant is incorporated into a polymer; Japanese Patent Kokai Publication No. 63-153060 proposes a method in which an oxidizing agent is incorporated into a polymer; Japanese Patent Kokai Publication No. 63-127754 proposes a method in which an antioxidant is incorporated into a polymer; Japanese Patent Kokai Publication No. 63-272349 proposes a method in which a sulfur-containing reducing agent is incorporated into a polymer; Japanese Patent Kokai Publication No. 63-146964 proposes a method in which a metal chelating agent is incorporated into a polymer; Japanese Patent Kokai Publication No. 63-15266 proposes a method in which a radical chain inhibitor is incorporated into a polymer; Japanese Patent Kokai Publication No. 1-275661 proposes a method in which a phosphinic acid group- or phosphonic acid group-containing amine compound or a salt thereof is incorporated into a polymer; Japanese Patent Kokai Publication No. 64-29257 proposes a method in which a polyvalent metal oxide is incorporated into a polymer; and Japanese Patent Kokai Publications Nos. 2-255804 and 3-179008 propose a method in which a water-soluble chain transfer agent is allowed to coexist when polymerization is conducted. However, all of the above-enumerated methods have problems such that the deterioration of a gel cannot be sufficiently prevented, or that an effect on preventing the deterioration of a gel is largely dependent upon individuals' differences in body fluids. Moreover, the gel strength is hardly improved when any of the above methods is employed.

In view of the aforementioned situations in the prior art, an object of the present invention is to provide highly water-absorptive polymers which are improved both in the strength and stability of a gel after when water, in particular, a body fluid such as urine which is very different between individuals, is absorbed therein, without the water absorption capacity inherent in highly water-absorptive polymers being impaired.

SUMMARY OF THE INVENTION

The present inventors have found that the above object can be attained by incorporating a specific additive into a highly water-absorptive polymer, or by treating a highly water-absorptive polymer with a specific compound.

Thus, the present invention provides, in a first embodiment thereof, a highly water-absorptive polymer composition comprising:

(A) 100 parts by weight of a highly water-absorptive polymer having a crosslinked structure, comprising as its constituent a carboxyl group and/or a carboxylate group; and (B) 0.05 to 10 parts by weight of an additive selected from the group consisting of an oxalic acid (salt) compound, a sulfate of a metal selected from titanium, zirconium and vanadium, and a crystalline or noncrystalline, high-purity particulate titania having a mean particle diameter of 1 $\mu$m or less, a specific surface area of 10 $m^2/g$ or more as determined by the Brunauer-Emmett-Teller method, and, when crystalline, a crystal structure of a mixed type of rutile and anatase.

The present invention provides, in a second embodiment thereof, a method for producing a highly water-absorptive polymer having enhanced gel strength, which comprises treating with an alkoxytitanium a highly water-absorptive polymer having a crosslinked structure, comprising as its constituent a carboxyl group and/or a carboxylate group.

The highly water-absorptive polymer compositions according to the present invention, and the highly water-absorptive polymers obtained by the method of the present invention are simultaneously improved in the gel strength, the stability of gel for a long time and "stickiness" on the surface of the gel, especially for the gel swollen with body fluids such as human urine or with an electrolytic solution, without the water absorption capacity inherent in highly water-absorptive polymers being impaired. Therefore, they can be advantageously used, in particular, in the fields of sanitary goods, and industrial, agricultural and horticultural materials for disposing strong electrolytic solutions.

Figure 1:
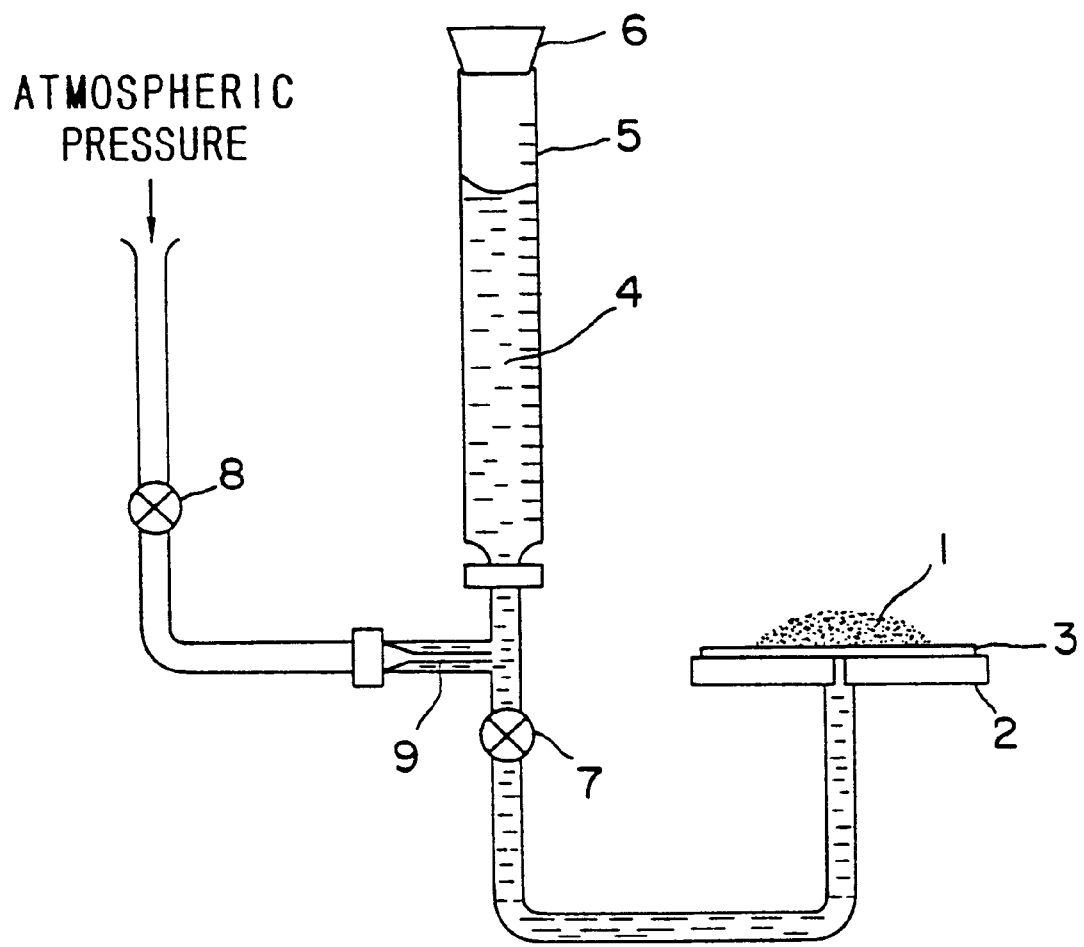
FIG. 1 is a schematic view of a device to be used to determine the rate of water absorption (under normal pressure) of a highly water-absorptive polymer.

Throughout the drawings, reference numeral 1 indicates a highly water-absorptive polymer (composition) (1 g); reference numeral 2, a support plate with a small hole; reference numeral 3, a nonwoven fabric; reference numeral 4, artificial urine; reference numeral 5, a burette; reference numeral 6, a rubber stopper; reference numerals 7 and 8, valves; reference numeral 9, an air inlet; reference numeral 10, a guide; and reference numeral 11, a weight.

DETAILED DESCRIPTION OF THE INVENTION

Highly Water-Absorptive Polymer

Any highly water-absorptive polymer can be used, irrespective of the type of the polymer and the polymerization method for preparing the polymer, as the highly water-absorptive polymer for use in the present invention, as long as it has a crosslinked structure, and comprises as its constituent a carboxyl group and/or carboxylate group. Preferable examples of such a polymer include a crosslinked polyacrylic acid salt, a crosslinked graft copolymer of starch and an acrylic acid salt, a saponified product of a crosslinked starch-acrylonitrile graft copolymer, a saponified product of a crosslinked acrylic ester-vinyl acetate copolymer, a crosslinked acrylic acid salt-acrylamide copolymer, and a saponified product of a crosslinked polyacrylonitrile. In addition to the above, polyethylene oxide crosslinked with acrylic acid, a crosslinked sodium carboxymethyl cellulose, a crosslinked copolymer of a salt of maleic anhydride and isobutylene, and a copolymer of an acrylic acid salt and a comonomer such as a maleic acid salt, an itaconic acid salt, a salt of 2-acrylamide-2-methylsulfonate, 2-acryloylethanesulfonic acid or 2-hydroxyethyl acrylate can be mentioned. The carboxylate group contained in the highly water-absorptive polymer may be of the type of an alkali metal salt, an alkaline earth metal salt, an ammonium salt, or the like. Of these, an alkali metal salt is preferred.

The above-described highly water-absorptive polymer can be obtained, in general, by polymerizing a polymerizable monomer having a carboxyl group and/or a carboxylate group, such as acrylic acid (or a salt thereof) or maleic anhydride (or a salt thereof) in the presence or absence of water, a radical polymerization initiator and a crosslinking agent by a known method such as an aqueous solution polymerization method, a solution polymerization method, or a reverse-phase suspension polymerization method. For instance, the polymer can be obtained by any one of the methods described in Japanese Patent Kokoku Publication No. 60-25045, Japanese Patent Application No. 59-210198, Japanese Patent Kokai Publications Nos. 57-158210 and 57-21405, Japanese Patent Kokoku Publication No. 53-46199, and Japanese Patent Kokai Publications Nos. 58-71907, 55-84304, 56-91837, 2-49002, 61-157513 and 62-62807. The crosslinking conducted during the polymerization is the internal crosslinking of the highly water-absorptive polymer, and it is different from the crosslinking which will be described later in the surface treatment of the polymer in both the operation and the nature. Thus, the internal crosslinking is to uniformly crosslink the inner portion of the polymer by uniformly dispersing a crosslinking agent in the monomer or polymer either before or during the polymerization. Even when a crosslinking agent is not used, the internal crosslinking may occur due to the so-called "self-crosslinking" of polymerizable monomers initiated by heat during the polymerization. As a crosslinking agent, use may be made of a compound which has two or more double bonds in its molecule and is copolymerizable with the polymerizable monomer; or a compound which has two or more functional groups in its molecule, which groups can react with a functional group such as a carboxyl group and/or carboxylate group contained in the polymerizable monomer, during the polymerization or in the treatment after the polymerization such as drying of the polymer. Examples of a crosslinking agent of the former type include N,N-methylene-bis(meth)acrylamide, ethylene glycol di(meth)acrylate, diethylene glycol di(meth)acrylate, polyethylene glycol di(meth)acrylate, propylene glycol di(meth)acrylate, polypropylene glycol di(meth)acrylate, diallyl phthalate, diallyl maleate, diallyl terephthalate, triallyl cyanurate, triallyl isocyanurate and triallyl phosphate. Examples of a crosslinking agent of the latter type include ethylene glycol diglycidyl ether, polyethylene glycol glycidyl ether, and a di- or polyglycidyl ether of an aliphatic polyhydric alcohol. In addition, N-methylol acrylamide and glycidyl (meth) acrylate can be mentioned as crosslinking agents which have the functions both of the former and the latter types.

When the polymerization is completed, the above-described highly water-absorptive polymer is, in general, obtained as a water-containing gel. This water-containing gel is usually dehydrated as it is, or by azeotropy with an inert solvent, and finally dried. The resultant is subjected, according to necessity, to pulverization, classification or the like to obtain a final product.

The highly water-absorptive polymer for use in the present invention may be one which has undergone a surface crosslinking or modification treatment during the above-described production processes, or after the final product is obtained.

Any crosslinking agent can be used for the surface crosslinking of the highly water-absorptive polymer as long as it has two or more functional groups which can react with a carboxyl group and/or a carboxylate group. For example, a polydiglycidyl ether compound, a haloepoxy compound, an aldehyde compound, an isocyanate compound or the like can be used as the crosslinking agent, and a polydiglycidyl ether compound is commonly used. There is no particular limitation on the amount of the crosslinking agent used. In general, however, it is used in the range of 0.005 to 5.0% by weight based on the polymer.

As an agent usable for the surface modification of the polymer, mention may be made of a silane compound represented by the following general formula:

$X(R)_m Si(Y)_{3-m}$ wherein X represents a functional group which can react with the carboxyl group and/or the carboxylate group contained in the highly water-absorptive polymer, R represents a hydrocarbon group, Y represents a hydrolyzable group, and m is 0, 1 or 2.

Specific examples of the silane compound having the above formula include

γ-glycidoxypropyltrimethoxysilane,
γ-glycidoxypropylmethyldiethoxysilane,
β-(3,4-epoxycyclohexyl)ethyltrimethoxysilane,
γ-(2-aminoethyl)aminopropyltrimethoxysilane,
γ-(2-aminoethyl)aminopropylmethyldimethoxysilane,
γ-aminopropyltriethoxysilane,
N-phenyl-γ-aminopropyltrimethoxysilane,
γ-mercaptopropyltrimethoxysilane,
γ-mercaptopropylmethyldimethoxysilane,
γ-chloropropyltrimethoxysilane,
γ-chloropropylmethyldimethoxysilane and octadecyldimethyl[3-(trimethoxysilyl)propyl] ammonium chloride.

There is no particular limitation on the amount of the above silane compound used. In general, however, it is in the range of 0.001 to 10.0% by weight based on the polymer.

The mean particle diameter of the highly water-absorptive polymer for use in the present invention is, in general, from 10 to 2,000 μm, preferably from 50 to 1,000 μm.

Oxalic Acid (Salt) Compound

Oxalic acid, or any metallic salt, double salt or organic compound based on oxalic acid can be used as the oxalic acid (salt) compound for use in the present invention. Specific examples of such a compound include oxalic acid, sodium oxalate, ammonium oxalate, zinc oxalate, potassium zinc oxalate, aluminum oxalate, ammonium aluminum oxalate, sodium aluminum oxalate, potassium antimony oxalate, uranyl oxalate, ammonium uranyl oxalate, potassium uranyl oxalate, calcium oxalate, silver oxalate, chromium oxalate, potassium chromium oxalate, cobalt oxalate, zirconium oxalate, mercury oxalate, ammonium mercury oxalate, ammonium hydrogenoxalate, potassium hydrogenoxalate, sodium hydrogenoxalate, barium hydrogenoxalate, tin oxalate, strontium oxalate, cesium oxalate, cerium oxalate, copper oxalate, iron oxalate, manganese oxalate, titanyl oxalate, ammonium titanyl oxalate, potassium oxalate titanate, sodium oxalate titanate, ammonium oxalate titanate, rubidium oxalate titanate, ammonium iron oxalate, potassium iron oxalate, potassium copper oxalate, lead oxalate, nickel oxalate, potassium nickel oxalate, vanadium oxalate, barium oxalate, bismuth oxalate, beryllium oxalate, magnesium oxalate, manganese oxalate, lithium oxalate, aniline oxalate, oxalic amide, dimethyl oxalate, diethyl oxalate, dinitrile oxalate, dihydrazide oxalate, urea oxalate and hydroxyammonium oxalate. The above-enumerated oxalic acid (salt) compounds can be used either singly or in combination of two or more. Of these compounds, oxalic acid, potassium oxalate, sodium oxalate, potassium oxalate titanate, sodium oxalate titanate and ammonium oxalate titanate are particularly preferred.

The amount of the oxalic acid (salt) compound used varies depending upon the type, properties and mean particle diameter of the highly water-absorptive polymer used. However, in general, it is from 0.05 to 10 parts by weight, preferably from 0.1 to 5 parts by weight per 100 parts by weight of the highly water-absorptive polymer. When the oxalic acid (salt) compound is used in combination with a polyvalent metal compound as described later, the total amount of the two should fall within the above ranges. In the case where the above amount is less than 0.05 parts by weight, the intended effects cannot be sufficiently attained. On the other hand, the use of an amount in excess of 10 parts by weight will not appreciably increase the intended effects.

Most of the above-described oxalic acid (salt) compounds are in the state of powder at room temperature under normal pressure. When the compound is used in the form of powder, it is preferred that the mean particle diameter thereof be as small as 10 μm or less, particularly 1 μm or less.

Polyvalent Metal Compound

Any metallic salt, double salt or organic compound based on a metal having a valence of 2 or more can be used as the polyvalent metal compound. When the polyvalent metal compound is used in the present invention, it should be used together with the above oxalic acid (salt) compound. Of such polyvalent metal compounds, oxides and sulfates are preferred. Specific examples of such compounds include silicon oxide, magnesium oxide, aluminum oxide, calcium oxide, titanium oxide, vanadium oxide, chromium oxide, manganese oxide, iron oxide, nickel oxide, cobalt oxide, copper oxide, zinc oxide, zirconium oxide, tungsten oxide, magnesium sulfate, calcium sulfate, aluminum sulfate, barium sulfate, titanium sulfate, titanyl sulfate, zirconium sulfate, vanadium sulfate, vanadyl sulfate, chromium sulfate, manganese sulfate, iron sulfate, cobalt sulfate, nickel sulfate, copper sulfate, zinc sulfate and aluminum sulfate. Of these compounds, oxides and sulfates of a metal selected from silicon, titanium, zirconium and vanadium, such as silicon oxide, titanium oxide, vanadium oxide, zirconium oxide, titanium sulfate, titanyl sulfate, zirconium sulfate and vanadyl sulfate are particularly preferred in the present invention.

The above polyvalent metal compound is used in such an amount that the total amount of the polyvalent metal compound and the oxalic acid (salt) compound is from 0.05 to 10 parts by weight, preferably from 0.1 to 5 parts by weight per 100 parts by weight of the highly water-absorptive polymer. The blend ratio (weight basis) of the oxalic acid (salt) compound to the polyvalent metal compound is from 10:90 to 90:10, preferably from 30:70 to 70:30.

When the above polyvalent metal compound is used in the form of powder, it is preferred that the mean particle diameter of the powder be as small as 10 μm or less, particularly 1 μm or less.

Metal Sulfate

The metal sulfate for use in the present invention is a sulfate of a metal selected from titanium, zirconium and vanadium. Specific examples include titanium sulfate, titanyl sulfate, zirconium sulfate and vanadyl sulfate. Sulfates of a polyvalent metal other than the above-mentioned ones, for example, a divalent metal such as magnesium, calcium, barium or zinc, or a trivalent metal such as aluminum or iron can only produce very small effects, so that they cannot attain the object of the present invention.

The amount of the metal sulfate to be used varies depending upon the type, properties, and mean particle diameter of the highly water-absorptive polymer used. However, it is generally from 0.05 to 10 parts by weight, preferably from 0.1 to 5 parts by weight per 100 parts by weight of the highly water-absorptive polymer. When the amount is less than 0.05 parts by weight, the intended effects cannot be attained sufficiently. On the other hand, even when the amount is in excess of 10 parts by weight, the effects attained are not significantly enhanced.

When the metal sulfate is used in the form of powder, it is preferred that the mean particle diameter be as small as 10 μm or less, particularly 1 μm or less.

High-Purity Particulate Titania

The high-purity particulate titania for use in the present invention is limited to one having a specified large specific surface area, being noncrystalline or having a specific crystal structure.

Specifically, the high-purity particulate titania is one having a mean particle diameter of 1 μm or less, preferably 0.01 to 0.1 μm, and a specific surface area of 10 $m^2/g$ or more, preferably 30 $m^2/g$ or more as determined by the Brunauer-Emmett-Teller method, being a crystalline compound having a crystal structure of a mixed type of rutile and anatase, or a noncrystalline compound. In the case of a crystalline titania, it is preferable that the constitution ratio (weight basis) of the rutile type to the anatase type be from 90/10 to 10/90, particularly from 80/20 to 20/80.

In the present invention, the term "high-purity" used with respect to the titania means that the pure titania content is 99% or more.

The amount of the high-purity particulate titania to be used is from 0.05 to 10 parts by weight, preferably from 0.1 to 5 parts by weight per 100 parts by weight of the highly water-absorptive polymer.

Production of Highly Water-Absorptive Polymer Composition

The highly water-absorptive polymer composition of the present invention may be produced in such a manner that a predetermined amount of the oxalic acid (salt) compound, a mixture of the oxalic acid (salt) compound and the polyvalent metal compound, the metal sulfate, or the high-purity particulate titania is added to and uniformly mixed with the highly water-absorptive polymer. The mixing may be conducted by any conventionally known method or means. It can be readily conducted by using a mixing apparatus that is usually employed for the mixing of powders, for example, a tank-type mixer having agitation elements, a fluid mixer, an air stream-type mixer, a vibrating mixer or a high-speed rotary paddle agitator. Further, as the case may be, the above additive can be added to and dispersed in the highly water-absorptive polymer during the step of polymerization, aging, dehydration, surface modification or granulation of the polymer.

The temperature at which the polymer and the additive are mixed is, in general, from room temperature to 150° C., preferably from room temperature to 50° C.

Alkoxytitanium

Any organic titanium compound having a reactive alkoxy group in its molecule can be used as the alkoxytitanium for use in the method of the present invention.

Specific examples of the alkoxytitanium include tetramethoxytitanium, tetraethoxytitanium, tetraisopropoxytitanium, tetrabutoxytitanium, tetrakis(2-ethylhexyloxy)titanium, tetrastearyloxytitanium, a tetraisopropoxytitanium polymer, a tetrabutoxytitanium polymer, diisopropoxybis(acetylacetonat)titanium, dibutoxybis(triethanolaminat)titanium, tributoxytitanium stearate, dihydroxybis(lactat)titanium and diisopropoxytitanium distearate. These compounds can be used either singly or in combination of two or more. Of these compounds, tetraisopropoxytitanium and dibutoxybis(triethanolaminat)titanium are preferred.

The amount of the alkoxytitanium used in the present invention varies depending upon the type of the polymer used. However, it is generally from 0.001 to 10% by weight, preferably from 0.05 to 3% by weight based on the polymer. When this amount is less than 0.001%, the stability of the highly water-absorptive polymer gel to body fluids cannot be sufficiently improved. On the other hand, when the amount is in excess of 10% by weight, the water absorption capacity of the highly water-absorptive polymer is impaired.

Treatment with Alkoxytitanium

The treatment of a highly water-absorptive polymer with an alkoxytitanium according to the method of the present invention can be conducted in various manners. For example, it can be conducted by a wet method in which an alkoxytitanium is added to a slurry of a highly water-absorptive polymer in a solvent, or by a dry method in which an alkoxytitanium is sprayed with dry air or nitrogen gas over a highly water-absorptive polymer while forcedly stirring the polymer.

Any inert solvent selected from hydrocarbons, alcohols and ethers can be used as the solvent for use in the above-described wet method.

Although the treatment with an alkoxytitanium according to the present invention is generally conducted to a water-containing polymer, it can also be conducted to a dry polymer.

The treatment temperature is, in general, from 10 to 180° C., preferably from 80 to 120° C.

The following examples further illustrate the present invention but are not intended to limit it.

In the examples, the following measurements were carried out:

Water absorption capacity 1 g of a highly water-absorptive polymer (composition) was placed in a 250-mesh nylon bag (10 cm×20 cm), and immersed in 1 liter of artificial urine for 30 minutes. Thereafter, the nylon bag was withdrawn, allowed to drain for 15 minutes, and weighed. The water absorption capacity was determined, by making a blank correction, as the weight of the artificial urine absorbed in 1 g of the highly water-absorptive polymer (composition). The formulation of the artificial urine used is as follows:

| Formulation of artificial urine: | |
|---|---|
| Urea | 1.94% |
| Sodium chloride | 0.80% |
| Calcium chloride | 0.06% |
| Magnesium sulfate | 0.11% |
| Pure water | 97.09% |

Rate of Water Absorption (Under Normal Pressure)

Measurement was carried out by using the device shown in FIG. 1. 1.0 g of a highly water-absorptive polymer (composition) 1 was placed on a nonwoven fabric 3 spread over a support plate 2 having a small hole, and brought into contact with the above-described artificial urine as shown in FIG. 1. The rate of water absorption (under normal pressure) was determined as the amount of the artificial urine absorbed in the highly water-absorptive polymer 1 for the first 10 minutes.

Rate of Water Absorption (Under Pressure)

Figure 2:
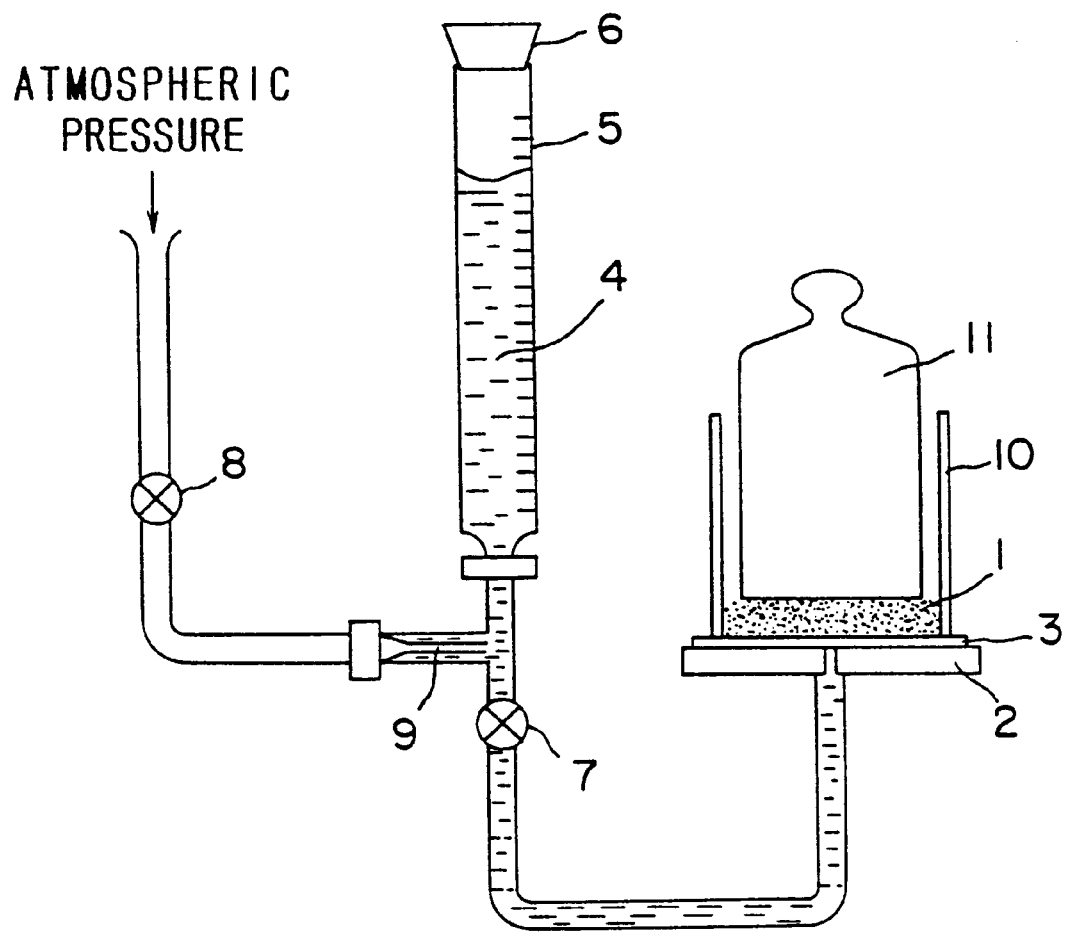
FIG. 2 is a schematic view of a device to be used to determine the rate of water absorption (under pressure) of a highly water-absorptive polymer.

Measurement was carried out by using the device shown in FIG. 2. 1.0 g of a highly water-absorptive polymer (composition) 1 was placed on a nonwoven fabric 3 spread over a support plate 2 having a small hole, and a guide 10 was provided around the sample polymer. A weight 11 (corresponding to 12 g/cm$^2$) was placed on the highly water-absorptive polymer 1. The polymer 1 was brought into contact with the above-described artificial urine as shown in FIG. 2. The rate of water absorption (under pressure) was determined as the amount of the artificial urine absorbed in the highly water-absorptive polymer 1 for the first 10 minutes.

Gel Strength a. 1 g of a highly water-absorptive polymer (composition) was impregnated with 25 g of human urine (a mixture of urines of 5 adults), and allowed to stand at 25° C. for 30 minutes. The gel thus obtained was placed on a rheometer (Model "NRM-2002J" manufactured by Fudo Kogyo), and the gel strength was determined as the strength at the time when a cell penetrated into the gel.

b. The procedure of the above "a" was repeated except that the human urine used in the above "a" was replaced by the same artificial urine as used in the above-described measurement of the water absorption capacity.

Stability of Gel

A sample which was the same as one used in the above-described measurement of the gel strength was prepared, and allowed to stand in a thermostatic bath at a preset temperature of 40° C. for 16 hours. Thereafter, the strength of the gel was measured by the above-described method to evaluate the stability of the gel. It is noted that when the data obtained from a plurality of runs are shown in the following Tables, the urine sample was changed at each run with consideration of individuals' differences in human urine.

Stickiness on Gel Surface

The "stickiness" of the swollen gel after the above measurement of the stability of gel was evaluated in accordance with the following standard, by touching it with fingers:

◯: The swollen gel has a dry feel.

Δ: The swollen gel is partially sticky.

x: The swollen gel is sticky, and the fingers are slimed.

The following highly water-absorptive polymers were used in Examples and Comparative Examples which will be described later.

Highly Water-Absorptive Polymer (A)

In a four-necked 5,000 ml round flask, equipped with a stirrer, a reflux condenser, a thermometer and a nitrogen gas supply tube was placed 1,210 g of cyclohexane. 9 g of sorbitan monostearate was added to the cyclohexane and dissolved therein, and dissolved oxygen was then expelled by blowing nitrogen gas into the flask.

Separately, 143.1 g of sodium hydroxide with 95% purity dissolved in 727.7 g of water was added to 350 g of acrylic acid placed in a 2,000 ml beaker while externally cooling with ice, thereby neutralizing 70% of the carboxyl groups. In this case, the concentration of the monomer in the aqueous solution corresponds to 35% by weight, as measured for the neutralized monomer. Subsequently, 0.37 g of N,N'-methylenebisacrylamide and 0.94 g of potassium persulfate were added to the solution, and dissolved therein. Dissolved oxygen was then expelled by blowing nitrogen gas into the solution.

The content of the 2000 ml beaker was added to the content of the four-necked round flask, followed by mixing under agitation. The internal temperature of the flask was raised in an oil bath while bubbling nitrogen gas. After the internal temperature reached approximately 60° C., it rose rapidly and finally reached 75° C. after several tens of minutes. While the internal temperature of the flask was maintained at 60 to 65° C., reaction was carried out for 3 hours with stirring at 145 rpm. When the stirring was stopped, wet polymer particles settled down on the bottom of the round flask. These particles could be easily separated from the cyclohexane phase by decantation.

The separated wet polymer was transferred into a vacuum dryer, and heated to a temperature of 90° C. to remove the extraneous cyclohexane and water therefrom, whereby 400 g of a highly water-absorptive polymer was obtained as a dry powder.

100 g of the dry polymer thus obtained was placed in a 500 ml egg plant-type flask, and to this was added 122.5 g of cyclohexane to obtain a slurry. While stirring the slurry, a dispersion of 0.44 g of γ-glycidoxypropyltrimethoxysilane in 22.5 g of water was added, and the mixture was stirred at room temperature for 30 minutes. Subsequently, the flask was placed in an oil bath at a temperature of 105° C. for 30 minutes. Thereafter, while the temperature of the oil bath was maintained at 105° C., the content of the flask was dried under reduced pressure. As a result, 95 g of a dry polymer was obtained.

Highly Water-Absorptive Polymer (B)

The procedure for the synthesis of the highly water-absorptive polymer (A) was repeated except that the γ-glycidoxypropyltrimethoxysilane was replaced by 0.8 g of ethylene glycol diglycidyl ether, whereby 95 g of a dry polymer was obtained.

Highly Water-Absorptive Polymer (C)

A crosslinked starch/acrylic acid salt graft polymer, "Sun-wet IM-1000" manufactured by Sanyo Chemical Industries, Ltd., was used as the highly water-absorptive polymer (C).

Highly Water-Absorptive Polymer (D)

A crosslinked polyacrylic acid salt, "Alialic CAW-4" manufactured by Nippon Shokubai Kagaku Kogyo Co., Ltd., was used as the highly water-absorptive polymer (D).

Highly Water-Absorptive Polymer (E)

Out of 400 g of the highly water-absorptive polymer obtained during the synthesis of the highly water-absorptive polymer (A), 100 g of the polymer was taken, and added to a solution consisting of 5 g of calcium nitrate, 80 g of ethyl alcohol and 10 g of water. The mixture was stirred at 25° C. for 5 minutes, and then filtered. The powder thus obtained was dried at 90° C. under reduced pressure for 3 hours, whereby 95 g of a dry polymer was obtained.

EXAMPLES I-1 TO I-23

High-purity particulate titania was added to and uniformly mixed with each of the above-described highly water-absorptive polymers (A), (B), (C) and (D), thereby obtaining highly water-absorptive polymer compositions.

The types and amounts of the highly water-absorptive polymers and of the high-purity particulate titanias are as shown in Table I-1.

The highly water-absorptive polymer compositions obtained were subjected to the above-described measurements. The results are shown in Table I-3.

COMPARATIVE EXAMPLES I-1 TO I-4

The highly water-absorptive polymers (A), (B), (C) and (D), to which high-purity particulate titania was not added, were subjected to the above-described measurements. The types of the polymers used, and the results of the measurements are shown in Tables I-2 and I-3, respectively.

COMPARATIVE EXAMPLES I-5 TO I-22

Highly water-absorptive polymer compositions were obtained by using the highly water-absorptive polymers and high-purity particulate titanias of which types are shown in Table I-2, in accordance with the formulations shown in the table. The compositions obtained were subjected to the above-described measurements. The results are shown in Table I-3.

TABLE I-1

| | | | | High-purity particulate titania | | | |
|---|---|---|---|---|---|---|---|
| Example No. | | Polymer and its amount used | Type | Mean particle diameter ($\mu m$) | Specific surface area ($m^2/g$) | Crystal structure | Amount (g) |
| Example | I-1 | Highly water-absorptive polymer (A) 100 g | Trade name: Aerosil P-25 (manufactured by Nippon Aerosil Co., Ltd.) | 0.021 | 50 | Anatase/rutile = 75/25 | 0.3 |
| | I-2 | Highly water-absorptive polymer (A) 100 g | Trade name: Aerosil P-25 (manufactured by Nippon Aerosil Co., Ltd.) | 0.021 | 50 | Anatase/rutile = 75/25 | 0.5 |
| | I-3 | Highly water-absorptive polymer (A) 100 g | Trade name: Aerosil P-25 (manufactured by Nippon Aerosil Co., Ltd.) | 0.021 | 50 | Anatase/rutile = 75/25 | 1.0 |
| | I-4 | Highly water-absorptive polymer (A) 100 g | Trade name: Aerosil P-25 (manufactured by Nippon Aerosil Co., Ltd.) | 0.021 | 50 | Anatase/rutile = 75/25 | 3.0 |
| | I-5 | Highly water-absorptive polymer (A) 100 g | Trade name: Idemitsu Titania IT-S (manufactured by Idemitsu Kosan Co., Ltd.) | 0.017 | 135 | Noncrystalline | 0.5 |
| | I-6 | Highly water-absorptive polymer (A) 100 g | Trade name: Idemitsu Titania IT-S (manufactured by Idemitsu Kosan Co., Ltd.) | 0.017 | 135 | Noncrystalline | 1.0 |
| | I-7 | Highly water-absorptive polymer (A) 100 g | Titanium Oxide SJ-35B (trial product manufactured by Mitsubishi Petrochemical Co., Ltd.) | 0.53 | 37 | Anatase/rutile = 35/65 | 1.0 |
| | I-8 | Highly water-absorptive polymer (A) 100 g | Titanium Oxide SJ-35B (trial product manufactured by Mitsubishi Petrochemical Co., Ltd.) | 0.53 | 37 | Anatase/rutile = 35/65 | 3.0 |
| | I-9 | Highly water-absorptive polymer (B) 100 g | Trade name: Aerosil P-25 (manufactured by Nippon Aerosil Co., Ltd.) | 0.021 | 50 | Anatase/rutile = 75/25 | 0.5 |
| | I-10 | Highly water-absorptive polymer (B) 100 g | Trade name: Aerosil P-25 (manufactured by Nippon Aerosil Co., Ltd.) | 0.021 | 50 | Anatase/rutile = 75/25 | 1.0 |
| | I-11 | Highly water-absorptive polymer (B) 100 g | Trade name: Aerosil P-25 (manufactured by Nippon Aerosil Co., Ltd.) | 0.021 | 50 | Anatase/rutile = 75/25 | 3.0 |
| | I-12 | Highly water-absorptive polymer (B) 100 g | Trade name: Idemitsu Titania IT-S (manufactured by Idemitsu Kosan Co., Ltd.) | 0.017 | 135 | Noncrystalline | 1.0 |
| | I-13 | Highly water-absorptive polymer (B) 100 g | Trade name: Idemitsu Titania IT-S (manufactured by Idemitsu Kosan Co., Ltd.) | 0.017 | 135 | Noncrystalline | 3.0 |
| Example | I-14 | Highly water-absorptive polymer (C) 100 g | Trade name: Aerosil P-25 (manufactured by Nippon Aerosil Co., Ltd.) | 0.021 | 50 | Anatase/rutile = 75/25 | 0.5 |
| | I-15 | Highly water-absorptive polymer (C) 100 g | Trade name: Aerosil P-25 (manufactured by Nippon Aerosil Co., Ltd.) | 0.021 | 50 | Anatase/rutile = 75/25 | 1.0 |
| | I-16 | Highly water-absorptive polymer (C) 100 g | Trade name: Aerosil P-25 (manufactured by Nippon Aerosil Co., Ltd.) | 0.021 | 50 | Anatase/rutile = 75/25 | 3.0 |

TABLE I-1-continued

|  |  | High-purity particulate titania | | | | |
|---|---|---|---|---|---|---|
| Example No. | Polymer and its amount used | Type | Mean particle diameter ($\mu$m) | Specific surface area ($m^2/g$) | Crystal structure | Amount (g) |
| I-17 | Highly water-absorptive polymer (C) 100 g | Trade name: Idemitsu Titania IT-S (manufactured by Idemitsu Kosan Co., Ltd.) | 0.017 | 135 | Noncrystalline | 1.0 |
| I-18 | Highly water-absorptive polymer (C) 100 g | Trade name: Idemitsu Titania IT-S (manufactured by Idemitsu Kosan Co., Ltd.) | 0.017 | 135 | Noncrystalline | 3.0 |
| I-19 | Highly water-absorptive polymer (D) 100 g | Trade name: Aerosil P-25 (manufactured by Nippon Aerosil Co., Ltd.) | 0.021 | 50 | Anatase/rutile = 75/25 | 0.5 |
| I-20 | Highly water-absorptive polymer (D) 100 g | Trade name: Aerosil P-25 (manufactured by Nippon Aerosil Co., Ltd.) | 0.021 | 50 | Anatase/rutile = 75/25 | 1.0 |
| I-21 | Highly water-absorptive polymer (D) 100 g | Trade name: Aerosil P-25 (manufactured by Nippon Aerosil Co., Ltd.) | 0.021 | 50 | Anatase/rutile = 75/25 | 3.0 |
| I-22 | Highly water-absorptive polymer (D) 100 g | Trade name: Idemitsu Titania IT-S manufactured by Idemitsu Kosan Co., Ltd.) | 0.017 | 135 | Noncrystalline | 1.0 |
| I-23 | Highly water-absorptive polymer (D) 100 g | Trade name: Idemitsu Titania IT-S manufactured by Idemitsu Kosan Co., Ltd.) | 0.017 | 135 | Noncrystalline | 3.0 |

TABLE I-2

|  |  | High-purity particulate titania | | | | |
|---|---|---|---|---|---|---|
| Comp. Example No. | Polymer and its amount used | Type | Mean particle diameter ($\mu$m) | Specific surface area ($m^2/g$) | Crystal structure | Amount (g) |
| Comp. Ex. I-1 | Highly water-absorptive polymer (A) 100 g | — | — | — | — | — |
| I-2 | Highly water-absorptive polymer (B) 100 g | — | — | — | — | — |
| I-3 | Highly water-absorptive polymer (C) 100 g | — | — | — | — | — |
| I-4 | Highly water-absorptive polymer (D) 100 g | — | — | — | — | — |
| I-5 | Highly water-absorptive polymer (A) 100 g | Titanium Oxide SJ-30-2 (trial product manufactured by Mitsubishi Petrochemical Co., Ltd.) | 17.0 | 30 | Anatase/rutile = 25/75 | 1.0 |
| I-6 | Highly water-absorptive polymer (A) 100 g | Titanium Oxide SJ-30-2 (trial product manufactured by Mitsubishi Petrochemical Co., Ltd.) | 17.0 | 30 | Anatase/rutile = 25/75 | 2.0 |
| I-7 | Highly water-absorptive polymer (A) 100 g | Titanium Oxide SJ-30-3 (trial product manufactured by Mitsubishi Petrochemical Co., Ltd.) | 9.0 | 54 | Anatase/rutile = 25/75 | 1.0 |
| I-8 | Highly water-absorptive polymer (A) 100 g | Kronos KV-200 (manufactured by Titan Kogyo Kabushiki Kaisha) | 0.4 | 5 | Anatase/rutile = 20/80 | 1.0 |
| I-9 | Highly water-absorptive polymer (A) 100 g | Kronos KA-10 (manufactured by Titan Kogyo Kabushiki Kaisha) | 0.4 | 10 | Anatase/rutile = 100/0 | 1.0 |
| I-10 | Highly water-absorptive polymer (A) 100 g | Titanium Oxide (manufactured by Wako Pure Chemical Industries, Ltd.) | 0.5 | 10 | Anatase/rutile = 0/100 | 1.0 |
| I-11 | Highly water-absorptive polymer (A) 100 g | Titanium Oxide SJ-30-2 (trial product manufactured by Mitsubishi Petrochemical Co., Ltd.) | 17.0 | 30 | Anatase/rutile = 25/75 | 1.0 |
| I-12 | Highly water-absorptive polymer (A) 100 g | Kronos KA-200 (manufactured by Titan Kogyo Kabushiki Kaisha) | 0.4 | 5 | Anatase/rutile = 20/80 | 1.0 |

TABLE I-2-continued

|  |  |  | High-purity particulate titania | | | |
|---|---|---|---|---|---|---|
| Comp. Example No. | Polymer and its amount used | Type | Mean particle diameter ($\mu$m) | Specific surface area ($m^2$/g) | Crystal structure | Amount (g) |
| Comp. Ex. I-13 | Highly water-absorptive polymer (B) 100 g | Kronos KA-10 (manufactured by Titan Kogyo Kabushiki Kaisha) | 0.4 | 10 | Anatase/rutile = 100/0 | 1.0 |
| I-14 | Highly water-absorptive polymer (B) 100 g | Titanium Oxide (manufactured by Wako Pure Chemical Industries, Ltd.) | 0.5 | 10 | Anatase/rutile = 0/100 | 1.0 |
| I-15 | Highly water-absorptive polymer (C) 100 g | Titanium Oxide SJ-30-2 (trial product manufactured by Mitsubishi Petrochemical Co., Ltd.) | 17.0 | 30 | Anatase/rutile = 25/75 | 1.0 |
| I-16 | Highly water-absorptive polymer (C) 100 g | Kronos KV-200 (manufactured by Titan Kogyo Kabushiki Kaisha) | 0.4 | 5 | Anatase/rutile = 20/80 | 1.0 |
| I-17 | Highly water-absorptive polymer (C) 100 g | Kronos KA-10 (manufactured by Titan Kogyo Kabushiki Kaisha) | 0.4 | 10 | Anatase/rutile = 100/0 | 1.0 |
| I-18 | Highly water-absorptive polymer (C) 100 g | Titanium Oxide (manufactured by Wako Pure Chemical Industries, Ltd.) | 0.5 | 10 | Anatase/rutile = 0/100 | 1.0 |
| I-19 | Highly water-absorptive polymer (D) 100 g | Titanium Oxide SJ-30-3 (trial product manufactured by Mitsubishi Petrochemical Co., Ltd.) | 17.0 | 30 | Anatase/rutile = 25/75 | 1.0 |
| I-20 | Highly water-absorptive polymer (D) 100 g | Kronos KV-200 (manufactured by Titan Kogyo Kabushiki Kaisha) | 0.4 | 5 | Anatase/rutile = 20/80 | 1.0 |
| I-21 | Highly water-absorptive polymer (D) 100 g | Kronos KA-10 (manufactured by Titan Kogyo Kabushiki Kaisha) | 0.4 | 10 | Anatase/rutile = 100/0 | 1.0 |
| I-22 | Highly water-absorptive polymer (D) 100 g | Titanium Oxide (manufactured by Wako Pure Chemical Industries, Ltd.) | 0.5 | 10 | Anatase/rutile = 0/100 | 1.0 |

TABLE I-3

|  | Water absorption capacity (g/g polymer) | Rate of water absorption (g/g polymer) | | Gel strength ($g/cm^2$) | | Stability of gel ($g/cm^2$) | | "Stickiness" on gel surface | |
|---|---|---|---|---|---|---|---|---|---|
|  |  | under normal pressure | under pressure | Artificial urine | Urine of human adult | Artificial urine | Urine of human adult | Artificial urine | Urine of human adult |
| Example No. | | | | | | | | | |
| Example I-1 | 41 | 46.5 | 24.2 | 39.9 | 27.9 | 38.9 | 28.6 | ○ | Δ~○ |
| I-2 | 42 | 48.7 | 28.5 | 46.2 | 33.8 | 45.8 | 34.4 | ○ | ○ |
| I-3 | 42 | 48.4 | 27.5 | 98.6 | 72.6 | 96.5 | 71.2 | ○ | ○ |
| I-4 | 43 | 48.4 | 28.9 | 95.2 | 73.2 | 94.6 | 72.4 | ○ | ○ |
| I-5 | 42 | 48.0 | 28.0 | 50.2 | 33.2 | 41.4 | 30.6 | ○ | Δ~○ |
| I-6 | 42 | 47.5 | 27.2 | 86.2 | 67.1 | 85.1 | 65.6 | ○ | ○ |
| I-7 | 41 | 47.2 | 25.8 | 80.4 | 64.8 | 78.8 | 62.4 | Δ~○ | Δ~○ |
| I-8 | 42 | 47.4 | 26.5 | 81.5 | 65.7 | 79.2 | 64.4 | ○ | Δ~○ |
| I-9 | 36 | 40.0 | 22.6 | 39.9 | 30.2 | 31.9 | 24.4 | Δ~○ | Δ~○ |
| I-10 | 38 | 41.2 | 24.6 | 68.9 | 57.3 | 60.1 | 54.7 | ○ | ○ |
| I-11 | 38 | 40.8 | 25.8 | 72.4 | 59.8 | 64.1 | 53.7 | ○ | ○ |
| I-12 | 37 | 39.6 | 22.1 | 59.7 | 48.2 | 58.2 | 40.9 | ○ | Δ~○ |
| I-13 | 37 | 40.8 | 24.6 | 60.0 | 49.9 | 59.7 | 44.7 | ○ | ○ |
| I-14 | 30 | 24.6 | 6.4 | 10.6 | 8.2 | 8.4 | 6.6 | Δ | Δ~X |
| I-15 | 31 | 26.4 | 7.5 | 24.2 | 18.7 | 20.0 | 14.9 | Δ~○ | Δ |
| I-16 | 32 | 27.9 | 8.5 | 30.2 | 25.1 | 29.9 | 24.4 | ○ | Δ~○ |
| I-17 | 32 | 24.4 | 6.0 | 9.9 | 7.0 | 7.2 | 6.0 | Δ | Δ~X |
| I-18 | 31 | 24.9 | 7.7 | 18.2 | 14.6 | 14.1 | 9.9 | Δ~○ | Δ |
| I-19 | 36 | 49.9 | 24.4 | 40.5 | 32.4 | 33.4 | 25.0 | Δ~○ | Δ |
| I-20 | 37 | 51.2 | 25.5 | 57.2 | 50.0 | 62.1 | 49.1 | ○ | Δ~○ |
| I-21 | 36 | 50.8 | 28.2 | 79.5 | 52.4 | 65.2 | 51.3 | ○ | ○ |
| I-22 | 36 | 49.6 | 27.4 | 62.3 | 46.3 | 56.6 | 41.1 | Δ~○ | Δ |
| I-23 | 37 | 49.4 | 27.9 | 66.6 | 47.2 | 57.3 | 45.0 | ○ | Δ~○ |

TABLE I-3-continued

| | | Water absorption capacity (g/g polymer) | Rate of water absorption (g/g polymer) | | Gel strength (g/cm²) | | Stability of gel (g/cm²) | | "Stickiness" on gel surface | |
|---|---|---|---|---|---|---|---|---|---|---|
| | | | under normal pressure | under pressure | Artificial urine | Urine of human adult | Artificial urine | Urine of human adult | Artificial urine | Urine of human adult |
| Comparative Example No. | | | | | | | | | | |
| Comp.Ex. | I-1 | 41 | 42.5 | 18.0 | 18.4 | 14.7 | 9.5 | —*) | Δ | X |
| | I-2 | 35 | 32.0 | 17.4 | 16.0 | 12.8 | 7.2 | — | Δ~X | X |
| | I-3 | 30 | 13.0 | 4.2 | 6.2 | 5.0 | 3.3 | — | Δ~X | X |
| | I-4 | 36 | 49.0 | 22.0 | 17.4 | 14.0 | 8.8 | — | Δ~X | X |
| | I-5 | 41 | 43.2 | 16.7 | 20.4 | 16.3 | 12.1 | — | Δ | X |
| | I-6 | 41 | 44.0 | 15.8 | 31.4 | 25.1 | 20.2 | 4.2 | Δ | Δ~X |
| | I-7 | 41 | 41.8 | 17.5 | 22.2 | 18.0 | 14.4 | — | Δ | X |
| | I-8 | 40 | 42.0 | 17.0 | 19.4 | 15.2 | 11.1 | — | Δ | X |
| | I-9 | 40 | 42.5 | 18.0 | 18.2 | 14.4 | 10.7 | — | Δ | X |
| | I-10 | 39 | 42.3 | 17.5 | 14.7 | 10.3 | 8.7 | — | Δ~X | X |
| | I-11 | 35 | 33.2 | 16.5 | 18.8 | 15.9 | 10.0 | — | Δ~X | X |
| | I-12 | 36 | 32.5 | 15.4 | 17.7 | 14.8 | 9.9 | — | Δ~X | X |
| | I-13 | 34 | 32.0 | 15.8 | 15.8 | 13.6 | 8.4 | — | Δ~X | X |
| | I-14 | 33 | 32.2 | 15.0 | 13.3 | 9.5 | 7.7 | — | Δ~X | X |
| | I-15 | 31 | 13.8 | 4.0 | 8.4 | 6.0 | 5.2 | — | Δ~X | X |
| | I-16 | 31 | 13.6 | 3.8 | 7.4 | 5.9 | 3.7 | — | Δ~X | X |
| | I-17 | 30 | 14.0 | 4.0 | 6.9 | 5.2 | 3.3 | — | Δ~X | X |
| | I-18 | 28 | 14.5 | 4.1 | 5.4 | 4.0 | 2.5 | — | Δ~X | X |
| | I-19 | 36 | 49.2 | 20.6 | 20.0 | 15.1 | 12.6 | — | Δ~X | X |
| | I-20 | 36 | 49.5 | 20.9 | 19.2 | 14.3 | 10.6 | — | Δ~X | X |
| | I-21 | 36 | 49.0 | 21.0 | 18.6 | 14.0 | 9.5 | — | Δ~X | X |
| | I-22 | 34 | 49.0 | 21.2 | 16.8 | 12.5 | 7.9 | — | Δ~X | X |

—*)immeasurable because the swollen gel was in a semifluid state.

EXAMPLES II-1 TO II-24

A metal sulfate was added to and uniformly mixed with each of the above-described highly water-absorptive polymers (A), (B), (C) and (D) in a twin-cylinder mixer (Model "S-5", manufactured by Tsutsui Rikagaku Kikai Co., Ltd.) at room temperature for 30 minutes, whereby highly water-absorptive polymer compositions were obtained.

The types and amounts of the highly water-absorptive polymers and of the metal sulfate are as shown in Table II-1.

The highly water-absorptive polymer compositions obtained were subjected to the above-described measurements. The results are shown in Table II-2.

COMPARATIVE EXAMPLES II-1 TO II-7

The above-described highly water-absorptive polymers (A), (B), (C) and (D), to which a metal sulfate was not added (Comparative Examples II-1, II-2, II-3 and II-4, respectively), and compositions obtained by adding, as a metal sulfate, 1 g of magnesium sulfate, 1 g of calcium sulfate, or 1 g of aluminum sulfate to 100 g of the highly water-absorptive polymer (A) (Comparative Examples II-5, II-6 and II-7, respectively) were subjected to the above-described measurements. The results are shown in Table II-2.

TABLE II-1

| Example No. | | Polymer and its amount used | Sulfated compound of a metal and its amount added | |
|---|---|---|---|---|
| Example | II-1 | Highly water-absorptive polymer (A) 100 g | Titanium sulfate | 0.5 |
| | II-2 | Highly water-absorptive polymer (A) 100 g | Titanium sulfate | 1.0 |
| | II-3 | Highly water-absorptive polymer (A) 100 g | Titanium sulfate | 2.0 |
| | II-4 | Highly water-absorptive polymer (A) 100 g | Titanyl sulfate | 0.5 |
| | II-5 | Highly water-absorptive polymer (A) 100 g | Titanyl sulfate | 1.0 |
| | II-6 | Highly water-absorptive polymer (A) 100 g | Titanyl sulfate | 2.0 |
| | II-7 | Highly water-absorptive polymer (A) 100 g | Zirconium sulfate | 0.5 |
| | II-8 | Highly water-absorptive polymer (A) 100 g | Zirconium sulfate | 1.0 |
| | II-9 | Highly water-absorptive polymer (A) 100 g | Zirconium sulfate | 2.0 |
| | II-10 | Highly water-absorptive polymer (A) 100 g | Vanadyl sulfate | 0.5 |
| | II-11 | Highly water-absorptive polymer (A) 100 g | Vanadyl sulfate | 1.0 |
| | II-12 | Highly water-absorptive polymer (A) 100 g | Vanadyl sulfate | 2.0 |
| | II-13 | Highly water-absorptive polymer (B) 100 g | Titanium sulfate | 1.0 |
| | II-14 | Highly water-absorptive polymer (B) 100 g | Titanyl sulfate | 1.0 |
| | II-15 | Highly water-absorptive polymer (B) 100 g | Zirconium sulfate | 1.0 |
| | II-16 | Highly water-absorptive polymer (B) 100 g | Vanadyl sulfate | 1.0 |
| | II-17 | Highly water-absorptive polymer (C) 100 g | Titanium sulfate | 1.0 |
| | II-18 | Highly water-absorptive polymer (C) 100 g | Titanyl sulfate | 1.0 |
| | II-19 | Highly water-absorptive polymer (C) 100 g | Zirconium sulfate | 1.0 |
| | II-20 | Highly water-absorptive polymer (C) 100 g | Vanadyl sulfate | 1.0 |

TABLE II-1-continued

| Example No. | Polymer and its amount used | Sulfated compound of a metal and its amount added | |
|---|---|---|---|
| II-21 | Highly water-absorptive polymer (D) 100 g | Titanium sulfate | 1.0 |
| II-22 | Highly water-absorptive polymer (D) 100 g | Titanyl sulfate | 1.0 |
| II-23 | Highly water-absorptive polymer (D) 100 g | Zirconium sulfate | 1.0 |
| II-24 | Highly water-absorptive polymer (D) 100 g | Vanadyl sulfate | 1.0 |

TABLE II-2

| | Example No. | Water absorption capacity (g/g polymer) | Gel strength <Urine of human adult> (g/cm$^2$) | Stability of gel <Urine of human adult> (g/cm$^2$) | | | | | | "Stickiness" on gel surface <Urine of human adult> | | | | |
|---|---|---|---|---|---|---|---|---|---|---|---|---|---|---|
| | | | | RUN 1 | RUN 2 | RUN 3 | RUN 4 | RUN 5 | Average | RUN 1 | RUN 2 | RUN 3 | RUN 4 | RUN 5 |
| Example | II-1 | 41 | 18.0 | 9.5 | 6.8 | 5.9 | 5.2 | 14.4 | 8.4 | Δ~○ | Δ~○ | Δ~○ | Δ | ○ |
| | II-2 | 41 | 27.1 | 24.2 | 10.6 | 12.4 | 14.4 | 9.8 | 14.3 | ○ | Δ~○ | ○ | ○ | Δ~○ |
| | II-3 | 40 | 29.6 | 10.2 | 12.8 | 24.6 | 18.6 | 20.9 | 17.4 | ○ | Δ~○ | ○ | ○ | ○ |
| | II-4 | 41 | 15.6 | 5.1 | 8.8 | 4.9 | g.4 | 10.1 | 7.7 | Δ | Δ~○ | Δ | Δ~○ | Δ~○ |
| | II-5 | 41 | 19.9 | 7.7 | 6.2 | 7.0 | 14.1 | 5.4 | 8.1 | Δ~○ | Δ~○ | Δ~○ | ○ | Δ~○ |
| | II-6 | 4a | 23.6 | la.2 | 20.7 | 9.0 | 17.5 | 19.3 | 15.3 | Δ~○ | ○ | Δ~○ | ○ | ○ |
| | II-7 | 42 | 20.1 | 8.8 | 14.4 | 13.6 | 18.8 | 17.9 | 14.7 | Δ | Δ~○ | Δ~○ | ○ | Δ~○ |
| | II-8 | 41 | 28.0 | 14.4 | 21.2 | 13.8 | 22.4 | 20.6 | 18.5 | Δ~○ | ○ | Δ~○ | ○ | ○ |
| | II-9 | 40 | 31.8 | 27.9 | 20.6 | 28.2 | 23.5 | 25.5 | 25.1 | ○ | ○ | ○ | ○ | ○ |
| | II-10 | 41 | 16.1 | 9.9 | 8.7 | 7.7 | 4.4 | 6.5 | 7.4 | Δ~○ | Δ~○ | Δ~○ | Δ | Δ |
| | II-11 | 41 | 22.9 | 12.2 | 20.0 | 13.1 | 9.5 | 19.5 | 14.9 | Δ~○ | ○ | Δ~○ | Δ~○ | ○ |
| | II-12 | 41 | 30.0 | 14.0 | 24.4 | 20.6 | 27.2 | 18.2 | 20.9 | Δ~○ | ○ | ○ | ○ | Δ~○ |
| | II-13 | 35 | 19.9 | 15.2 | 9.2 | 6.2 | 8.7 | 14.9 | 10.8 | ○ | Δ~○ | Δ | Δ~○ | ○ |
| | II-14 | 34 | 14.5 | 4.9 | 5.1 | 4.8 | 7.2 | 12.6 | 6.9 | Δ | Δ | Δ | Δ~○ | ○ |
| | II-15 | 36 | 21.1 | 16.7 | 15.8 | 10.2 | 14.4 | 9.7 | 13.4 | ○ | ○ | Δ~○ | ○ | Δ~○ |
| | II-16 | 35 | 15.8 | 5.9 | 5.9 | 6.8 | 11.2 | 7.9 | 7.5 | Δ | Δ | Δ~○ | ○ | Δ~○ |
| | II-17 | 31 | 8.9 | 4.2 | 7.9 | 5.2 | 4.9 | 4.6 | 5.4 | Δ | Δ~○ | Δ | Δ | Δ |
| Example | II-18 | 30 | 6.6 | 4.4 | 5.2 | 4.6 | 2.4 | 3.8 | 4.1 | Δ | Δ | Δ | Δ~X | Δ |
| | II-19 | 31 | 9.4 | 8.2 | 3.8 | 4.2 | 4.6 | 7.9 | 5.7 | Δ~○ | Δ | Δ | Δ | Δ~○ |
| | II-20 | 30 | 7.2 | 6.6 | 5.6 | 4.6 | 6.0 | 6.2 | 5.8 | Δ | Δ | Δ | Δ | Δ |
| | II-21 | 35 | 25.4 | 15.3 | 11.2 | 20.6 | 16.2 | 14.2 | 15.5 | Δ~○ | Δ~○ | ○ | Δ~○ | Δ~○ |
| | II-22 | 36 | 17.6 | 5.4 | 8.2 | g.6 | 14.4 | 13.2 | 10.2 | Δ | Δ~○ | Δ~○ | ○ | |
| | II-23 | 35 | 26.6 | 20.2 | 12.6 | 11.2 | 18.6 | 17.2 | 16.0 | ○ | Δ~○ | Δ~○ | ○ | |
| | II-24 | 36 | 20.1 | 16.4 | 11.2 | 14.9 | 10.6 | 8.6 | 12.3 | ○ | Δ~○ | ○ | Δ~○ | Δ~○ |
| Comp.Ex. | II-1 | 41 | 14.7 | —* | — | — | — | 3.5 | 0.7 | X | X | X | X | X |
| | II-2 | 35 | 12.8 | — | 0.6 | — | — | — | 0.1 | X | X | X | X | X |
| | II-3 | 30 | 5.0 | — | — | — | — | — | 0.0 | X | X | X | X | X |
| | II-4 | 36 | 14.0 | — | 5.4 | — | — | 0.2 | 1.1 | X | Δ~X | X | X | X |
| | II-5 | 41 | 14.9 | — | — | — | 2.8 | 2.2 | 1.0 | X | X | X | X | X |
| | II-6 | 40 | 15.2 | — | — | 2.9 | — | 3.6 | 1.3 | X | X | X | Δ~X | X |
| | II-7 | 40 | 15.0 | — | 2.9 | — | 2.6 | — | 1.1 | X | X | X | X | Δ~X |

*In the table, "—" means that the measurement was not able to be carried out because the swollen gel was in a semifluid state.

EXAMPLES III-1 TO III-24

An oxalic acid (salt) compound was added to and uniformly mixed with each one of the above-described highly water-absorptive polymers (A) to (E) in a twin-cylinder mixer (Model "S-5", manufactured by Tsutsui Rikagaku Kikai Co., Ltd.) at room temperature for 30 minutes, whereby highly water-absorptive polymer compositions were obtained.

The types and amounts of the highly water-absorptive polymers and of the oxalic acid (salt) compounds are as shown in Table III-1.

The highly water-absorptive polymer compositions obtained were subjected to the above-described measurements. The results are shown in Table III-2.

COMPARATIVE EXAMPLES III-1 TO III-5

The above-described highly water-absorptive polymers (A), (B), (E), (C) and (D), to which no oxalic acid (salt) compound was added (Comparative Examples III-1, III-2, III-3, III-4 and III-5, respectively), were subjected to the above-described measurements. The results are shown in Table III-2.

TABLE III-1

| | | Polymer and its amount used | Oxalic acid (salt) compound | Amount (g) |
|---|---|---|---|---|
| Example | III-1 | Highly water-absorptive polymer (A) 100 g | Oxalic acid | 0.5 |
| | III-2 | Highly water-absorptive polymer (A) 100 g | Oxalic acid | 1.0 |
| | III-3 | Highly water-absorptive polymer (A) 100 g | Oxalic acid | 2.0 |
| | III-4 | Highly water-absorptive polymer (A) 100 g | Potassium oxalate | 0.5 |
| | III-5 | Highly water-absorptive polymer (A) 100 g | Potassium oxalate | 1.0 |

TABLE III-1-continued

| | Polymer and its amount used | Oxalic acid (salt) compound | Amount (g) |
|---|---|---|---|
| III-6 | Highly water-absorptive polymer (A) 100 g | Potassium oxalate | 2.0 |
| III-7 | Highly water-absorptive polymer (A) 100 g | Potassium oxalate titanate | 0.5 |
| III-8 | Highly water-absorptive polymer (A) 100 g | Potassium oxalate titanate | 1.0 |
| III-9 | Highly water-absorptive polymer (A) 100 g | Potassium oxalate titanate | 2.0 |
| III-10 | Highly water-absorptive polymer (A) 100 g | Sodium oxalate | 1.0 |
| III-11 | Highly water-absorptive polymer (A) 100 g | Sodium oxalate titanate | 1.0 |
| III-12 | Highly water-absorptive polymer (B) 100 g | Oxalic acid | 1.0 |
| III-13 | Highly water-absorptive polymer (B) 100 g | Potassium oxalate | 1.0 |
| III-14 | Highly water-absorptive polymer (B) 100 g | Potassium oxalate titanate | 1.0 |
| III-15 | Highly water-absorptive polymer (E) 100 g | Oxalic acid | 1.0 |
| III-16 | Highly water-absorptive polymer (E) 100 g | Potassium oxalate | 1.0 |
| III-17 | Highly water-absorptive polymer (E) 100 g | Potassium oxalate titanate | 1.0 |
| III-18 | Highly water-absorptive polymer (C) 100 g | Oxalic acid | 1.0 |
| III-19 | Highly water-absorptive polymer (C) 100 g | Potassium oxalate | 1.0 |
| III-20 | Highly water-absorptive polymer (C) 100 g | Potassium oxalate titanate | 1.0 |
| III-21 | Highly water-absorptive polymer (D) 100 g | Oxalic acid | 1.0 |
| III-22 | Highly water-absorptive polymer (D) 100 g | Potassium oxalate | 1.0 |
| III-23 | Highly water-absorptive polymer (D) 100 g | Potassium oxalate titanate | 1.0 |
| III-24 | Highly water-absorptive polymer (A) 100 g | Ammonium oxalate titanate | 1.0 |

TABLE III-2

| | Example No. | Water absorption capacity (g/g polymer) | Gel strength <Urine of human adult> (g/cm$^2$) | Stability of gel <Urine of human adult> (g/cm$^2$) | | | | | | "Stickiness" on gel surface <Urine of human adult> | | | | |
|---|---|---|---|---|---|---|---|---|---|---|---|---|---|---|
| | | | | RUN 1 | RUN 2 | RUN 3 | RUN 4 | RUN 5 | Average | RUN 1 | RUN 2 | RUN 3 | RUN 4 | RUN 5 |
| Example | III-1 | 41 | 15.3 | 10.0 | 6.9 | 7.2 | 5.7 | 8.8 | 7.7 | ○ | △ | △ | △ | ○ |
| | III-2 | 41 | 16.3 | 11.1 | 12.9 | 5.0 | 10.9 | 7.2 | 9.4 | ○ | ○ | △ | ○ | △ |
| | III-3 | 40 | 20.2 | 16.6 | 14.9 | 12.6 | 14.0 | 11.2 | 13.9 | ○ | ○ | ○ | ○ | ○ |
| | III-4 | 42 | 17.8 | 15.0 | 11.3 | 12.1 | 10.0 | 9.9 | 11.7 | ○ | ○ | ○ | ○ | ○ |
| | III-5 | 41 | 20.6 | 10.8 | 20.0 | 11.1 | 17.8 | 19.9 | 15.9 | ○ | ○ | ○ | ○ | ○ |
| | III-6 | 41 | 42.9 | 40.6 | 17.8 | 10.2 | 20.8 | 19.9 | 21.9 | ○ | ○ | ○ | ○ | ○ |
| | III-7 | 40 | 38.2 | 16.6 | 28.2 | 30.9 | 30.2 | 18.9 | 25.0 | ○ | ○ | ○ | ○ | ○ |
| | III-8 | 41 | 45.9 | 40.2 | 26.6 | 40.2 | 35.3 | 28.0 | 34.1 | ○ | ○ | ○ | ○ | ○ |
| | III-9 | 40 | 53.4 | 58.49 | 50.8 | 36.2 | 25.4 | 48.5 | 42.9 | ○ | ○ | ○ | ○ | ○ |
| | III-10 | 41 | 15.4 | 9.5 | 5.8 | 6.6 | 10.9 | 11.4 | 8.8 | ○ | △ | △ | ○ | ○ |
| | III-11 | 42 | 39.5 | 30.8 | 29.5 | 31.4 | 30.7 | 28.8 | 30.2 | ○ | ○ | ○ | ○ | ○ |
| | III-12 | 35 | 14.4 | 7.7 | 6.9 | 12.9 | 11.1 | 6.6 | 9.0 | △ | △ | ○ | ○ | △ |
| | III-13 | 34 | 17.7 | 12.4 | 13.5 | 13.6 | 6.7 | 8.2 | 10.9 | ○ | ○ | ○ | △ | △ |
| | III-14 | 34 | 38.8 | 28.2 | 30.6 | 30.9 | 27.2 | 17.9 | 27.0 | ○ | ○ | ○ | ○ | ○ |
| | III-15 | 39 | 15.9 | 7.2 | 12.2 | 8.0 | 7.4 | 6.2 | 8.2 | △ | ○ | △ | △ | △ |
| | III-16 | 38 | 19.5 | 14.2 | 18.3 | 16.4 | 18.3 | 18.8 | 17.2 | ○ | ○ | ○ | ○ | ○ |
| | III-17 | 38 | 40.7 | 35.6 | 24.7 | 30.2 | 29.6 | 32.4 | 30.5 | ○ | ○ | ○ | ○ | ○ |
| | III-18 | 31 | 9.8 | 5.9 | 4.9 | 5.0 | 5.8 | 6.2 | 5.6 | △ | △ | △ | △ | △ |
| | III-19 | 31 | 12.7 | 7.2 | 8.2 | 6.9 | 5.8 | 4.9 | 6.6 | △ | △ | △ | △ | △ |
| | III-20 | 30 | 28.6 | 19.2 | 27.7 | 18.7 | 16.4 | 10.2 | 18.4 | ○ | ○ | ○ | ○ | △ |
| | III-21 | 36 | 15.0 | 9.8 | 10.0 | 6.2 | 4.9 | 4.4 | 7.1 | △ | ○ | △ | △ | △ |
| | III-22 | 36 | 17.4 | 9.8 | 18.2 | 14.4 | 10.9 | 9.2 | 12.5 | ○ | ○ | ○ | ○ | ○ |
| | III-23 | 36 | 40.0 | 20.6 | 31.4 | 19.9 | 33.3 | 32.6 | 27.6 | ○ | ○ | ○ | ○ | ○ |
| | III-24 | 40 | 43.2 | 35.8 | 25.5 | 40.2 | 32.4 | 26.8 | 31.5 | ○ | ○ | ○ | ○ | ○ |
| Comp.Ex. | III-1 | 41 | 14.7 | —* | — | — | — | 3.5 | 0.7 | X | X | X | X | X |
| | III-2 | 35 | 12.8 | — | 0.6 | — | — | — | 0.1 | X | X | X | X | X |
| | III-3 | 39 | 13.0 | — | — | 2.5 | — | — | 0.5 | X | X | X | X | X |
| | III-4 | 30 | 5.0 | — | — | — | — | — | 0.0 | X | X | X | X | X |
| | III-5 | 36 | 14.0 | — | 5.4 | — | — | 0.2 | 1.1 | X | X | X | X | X |

*In the table, "—" means that the measurement was not able to be carried out because the swollen gel was in a semifluid state.

EXAMPLES IV-1 TO IV-68

An oxalic acid (salt) compound and a polyvalent metal compound were added to and uniformly mixed with each of the above-described highly water-absorptive polymers (A), (B), (C) and (D) in a twin-cylinder mixer (Model "S-5", manufactured by Tsutsui Rikagaku Kikai Co., Ltd.) at room temperature for 30 minutes, whereby highly water-absorptive polymer compositions were obtained.

The types and amounts of the highly water-absorptive polymers, of the oxalic acid (salt) compounds and of the polyvalent metal compounds are as shown in Table IV-1.

The highly water-absorptive polymer compositions obtained were subjected to the above-described measurements. The results are shown in Tables IV-2 and IV-3.

TABLE IV-1

| Example No. | | Polymer and its amount used | Oxalic acid (salt) compound | Amount (g) | Polyvalent metal compound | Amount (g) |
|---|---|---|---|---|---|---|
| Example | IV-1 | High water-absorptive polymer (A) 100 g | Oxalic acid | 0.5 | Titania[1] | 0.5 |
| | IV-2 | High water-absorptive polymer (A) 100 g | Oxalic acid | 0.5 | Titania[2] | 0.5 |
| | IV-3 | High water-absorptive polymer (A) 100 g | Oxalic acid | 0.5 | Titania[3] | 0.5 |
| | IV-4 | High water-absorptive polymer (A) 100 g | Oxalic acid | 0.5 | Silica[1] | 0.5 |
| | IV-5 | High water-absorptive polymer (A) 100 g | Oxalic acid | 0.5 | Silica[2] | 0.5 |
| | IV-6 | High water-absorptive polymer (A) 100 g | Oxalic acid | 0.5 | Silica[3] | 0.5 |
| | IV-7 | High water-absorptive polymer (A) 100 g | Oxalic acid | 0.5 | Zirconium oxide[1] | 0.5 |
| | IV-8 | High water-absorptive polymer (A) 100 g | Oxalic acid | 0.5 | Zirconium oxide[2] | 0.5 |
| | IV-9 | High water-absorptive polymer (A) 100 g | Oxalic acid | 0.5 | Alumina[1] | 0.5 |
| | IV-10 | High water-absorptive polymer (A) 100 g | Oxalic acid | 0.5 | Alumina[2] | 0.5 |
| | IV-11 | High water-absorptive polymer (A) 100 g | Oxalic acid | 0.5 | Copper (II) oxide | 0.5 |
| | IV-12 | High water-absorptive polymer (A) 100 g | Oxalic acid | 0.5 | Titanium sulfate | 0.5 |
| | IV-13 | High water-absorptive polymer (A) 100 g | Oxalic acid | 0.5 | Titanyl sulfate | 0.5 |
| | IV-14 | High water-absorptive polymer (A) 100 g | Oxalic acid | 0.5 | Zirconium sulfate | 0.5 |
| | IV-15 | High water-absorptive polymer (A) 100 g | Oxalic acid | 0.5 | Vanadyl sulfate | 0.5 |
| | IV-16 | High water-absorptive polymer (A) 100 g | Potassium oxalate | 0.5 | Titania[1] | 0.5 |
| | IV-17 | High water-absorptive polymer (A) 100 g | Potassium oxalate | 0.5 | Titania[2] | 0.5 |
| | IV-18 | High water-absorptive polymer (A) 100 g | Potassium oxalate | 0.5 | Titania[3] | 0.5 |
| | IV-19 | High water-absorptive polymer (A) 100 g | Potassium oxalate | 0.5 | Silica[1] | 0.5 |
| | IV-20 | High water-absorptive polymer (A) 100 g | Potassium oxalate | 0.5 | Silica[2] | 0.5 |
| | IV-21 | High water-absorptive polymer (A) 100 g | Potassium oxalate | 0.5 | Silica[3] | 0.5 |
| | IV-22 | High water-absorptive polymer (A) 100 g | Potassium oxalate | 0.5 | Zirconium oxide[2] | 0.5 |
| | IV-23 | High water-absorptive polymer (A) 100 g | Potassium oxalate | 0.5 | Alumina[3] | 0.5 |
| Example | IV-24 | High water-absorptive polymer (A) 100 g | Potassium oxalate | 0.5 | Copper (II) oxide | 0.5 |
| | IV-25 | High water-absorptive polymer (A) 100 g | Potassium oxalate | 0.5 | Titanium sulfate | 0.5 |
| | IV-26 | High water-absorptive polymer (A) 100 g | Potassium oxalate | 0.5 | Titanyl sulfate | 0.5 |
| | IV-27 | High water-absorptive polymer (A) 100 g | Potassium oxalate | 0.5 | Zirconium sulfate | 0.5 |
| | IV-28 | High water-absorptive polymer (A) 100 g | Potassium oxalate | 0.5 | Vanadyl sulfate | 0.5 |
| | IV-29 | High water-absorptive polymer (A) 100 g | Potassium oxalate titanate | 0.5 | Titania[3] | 0.5 |
| | IV-30 | High water-absorptive polymer (A) 100 g | Potassium oxalate titanate | 0.5 | Silica[3] | 0.5 |
| | IV-31 | High water-absorptive polymer (A) 100 g | Potassium oxalate titanate | 0.5 | Zirconium oxide[3] | 0.5 |
| | IV-32 | High water-absorptive polymer (A) 100 g | Potassium oxalate titanate | 0.5 | Alumina[2] | 0.5 |
| | IV-33 | High water-absorptive polymer (A) 100 g | Potassium oxalate titanate | 0.5 | Copper (II) oxide | 0.5 |
| | IV-34 | High water-absorptive polymer (A) 100 g | Potassium oxalate titanate | 0.5 | Titanium sulfate | 0.5 |
| | IV-35 | High water-absorptive polymer (A) 100 g | Potassium oxalate titanate | 0.5 | Titanyl sulfate | 0.5 |
| | IV-36 | High water-absorptive polymer (A) 100 g | Potassium oxalate titanate | 0.5 | Zirconium sulfate | 0.5 |
| | IV-37 | High water-absorptive polymer (A) 100 g | Potassium oxalate titanate | 0.5 | Vanadyl sulfate | 0.5 |
| | IV-38 | High water-absorptive polymer (A) 100 g | Ammonium oxalate titanate | 0.5 | Titania[3] | 0.5 |
| | IV-39 | High water-absorptive polymer (A) 100 g | Ammonium oxalate titanate | 0.5 | Silica[3] | 0.5 |
| | IV-40 | High water-absorptive polymer (A) 100 g | Ammonium oxalate titanate | 0.5 | Zirconium oxide[3] | 0.5 |
| | IV-41 | High water-absorptive polymer (A) 100 g | Ammonium oxalate titanate | 0.5 | Alumina[2] | 0.5 |
| | IV-42 | High water-absorptive polymer (A) 100 g | Ammonium oxalate titanate | 0.5 | Copper (II) oxide | 0.5 |
| | IV-43 | High water-absorptive polymer (A) 100 g | Ammonium oxalate titanate | 0.5 | Titanium sulfate | 0.5 |
| | IV-44 | High water-absorptive polymer (A) 100 g | Ammonium oxalate titanate | 0.5 | Titanyl sulfate | 0.5 |
| | IV-45 | High water-absorptive polymer (A) 100 g | Ammonium oxalate titanate | 0.5 | Zirconium sulfate | 0.5 |
| | IV-46 | High water-absorptive polymer (A) 100 g | Ammonium oxalate titanate | 0.5 | Vanadyl sulfate | 0.5 |
| Example | IV-47 | High water-absorptive polymer (B) 100 g | Oxalic acid | 0.5 | Titania[3] | 0.5 |
| | IV-48 | High water-absorptive polymer (B) 100 g | Oxalic acid | 0.5 | Silica[3] | 0.5 |
| | IV-49 | High water-absorptive polymer (B) 100 g | Oxalic acid | 0.5 | Zirconium oxide[2] | 0.5 |
| | IV-50 | High water-absorptive polymer (B) 100 g | Oxalic acid | 0.5 | Alumina[1] | 0.5 |
| | IV-51 | High water-absorptive polymer (B) 100 g | Oxalic acid | 0.5 | Copper (II) oxide | 0.5 |
| | IV-52 | High water-absorptive polymer (B) 100 g | Oxalic acid | 0.5 | Titanium sulfate | 0.5 |
| | IV-53 | High water-absorptive polymer (B) 100 g | Oxalic acid | 0.5 | Titanyl sulfate | 0.5 |
| | IV-54 | High water-absorptive polymer (B) 100 g | Oxalic acid | 0.5 | Zirconium sulfate | 0.5 |
| | IV-55 | High water-absorptive polymer (B) 100 g | Oxalic acid | 0.5 | Vanadyl sulfate | 0.5 |
| | IV-56 | High water-absorptive polymer (C) 100 g | Oxalic acid | 0.5 | Titania[3] | 0.5 |
| | IV-57 | High water-absorptive polymer (C) 100 g | Oxalic acid | 0.5 | Titanyl sulfate | 0.5 |
| | IV-58 | High water-absorptive polymer (D) 100 g | Oxalic acid | 0.5 | Titania[2] | 0.5 |
| | IV-59 | High water-absorptive polymer (D) 100 g | Oxalic acid | 0.5 | Silica[1] | 0.5 |
| | IV-60 | High water-absorptive polymer (D) 100 g | Oxalic acid | 0.5 | Alumina[2] | 0.5 |
| | IV-61 | High water-absorptive polymer (A) 100 g | Potassium oxalate | 0.75 | Titania[1] | 0.75 |
| | IV-62 | High water-absorptive polymer (A) 100 g | Potassium oxalate | 1.0 | Titania[1] | 1.0 |
| | IV-63 | High water-absorptive polymer (A) 100 g | Potassium oxalate | 0.75 | Titania[3] | 0.75 |
| | IV-64 | High water-absorptive polymer (A) 100 g | Potassium oxalate | 1.0 | Titania[3] | 1.0 |
| | IV-65 | High water-absorptive polymer (A) 100 g | Oxalic acid | 0.1 | Titania[3] | 0.9 |
| | IV-66 | High water-absorptive polymer (A) 100 g | Oxalic acid | 0.9 | Titania[3] | 0.1 |
| | IV-67 | High water-absorptive polymer (A) 100 g | Potassium oxalate | 0.1 | Titania[3] | 0.9 |
| | IV-68 | High water-absorptive polymer (A) 100 g | Potassium oxalate | 0.9 | Titania[3] | 0.1 |

The details of the polyvalent metal compounds shown in Table IV-1 are as follows:

Titania[1]: "Titanium Oxide P-25" manufactured by Nippon Aerosil Co., Ltd., having a mean particle diameter of 0.021 μm and a specific surface area of 50 m²/g.

Titania[2]: "Taipake R-780" manufactured by Ishihara Kogyo Co., Ltd., having a mean particle diameter of 0.25 μm.

Titania[3]: "Kronos KR-460" manufactured by Titan Kogyo Kabushiki Kaisha, having a mean particle diameter of 0.2 to 0.4 μm.

Silica[1]: "Aerosil #380" manufactured by Nippon Aerosil Co., Ltd., having a mean particle diameter of 0.007 μm and a specific surface area of 380 $m^2/g$.

Silica[2]: "Silysia #770" manufactured by Fuji-Silysia Chemical, Ltd., having a mean particle diameter of 6.0 μm and a specific surface area of 700 $m^2/g$.

Silica[3]: "Carplex CS-500" manufactured by Shionogi & Co., Ltd., having a mean particle diameter of 2.1 μm.

Zirconium oxide[1]: Zirconium oxide manufactured by Nippon Aerosil Co., Ltd., having a mean particle diameter of 0.03 μm and a specific surface area of 40 $m^2/g$.

Zirconium oxide[2]: Guaranteed reagent manufactured by Wako Pure Chemical Industries, Ltd.

Alumina[1]: "Aluminum Oxide C" manufactured by Nippon Aerosil Co., Ltd., having a mean particle diameter of 0.013 μm and a specific surface area of 100 $m^2/g$.

Alumina[2]: Guaranteed reagent manufactured by Wako Pure Chemical Industries, Ltd.

TABLE IV-2

| Example No. | | Water absorption capacity (g/g polymer) | Gel strength <Urine of human adult> (g/cm²) | Stability of gel <Urine of human adult> (g/cm²) | | | | | | | | | |
|---|---|---|---|---|---|---|---|---|---|---|---|---|---|
| | | | | RUN 1 | RUN 2 | RUN 3 | RUN 4 | RUN 5 | RUN 6 | RUN 7 | RUN 8 | RUN 9 | RUN 10 | Average |
| Example | IV-1 | 42 | 48.4 | 38.2 | 40.2 | 42.4 | 36.5 | 38.5 | 36.2 | 40.1 | 39.8 | 36.2 | 33.6 | 38.2 |
| | IV-2 | 41 | 25.6 | 20.9 | 16.2 | 14.8 | 18.2 | 20.2 | 19.6 | 11.4 | 17.8 | 21.2 | 23.4 | 18.4 |
| | IV-3 | 41 | 19.9 | 10.5 | 14.7 | 11.4 | 12.3 | 12.6 | 9.8 | 14.4 | 15.6 | 14.8 | 12.4 | 12.9 |
| | IV-4 | 42 | 24.2 | 20.6 | 14.6 | 18.9 | 13.2 | 15.6 | 14.2 | 16.4 | 17.6 | 16.2 | 18.4 | 16.6 |
| | IV-5 | 42 | 22.6 | 16.6 | 19.4 | 10.4 | 11.2 | 17.4 | 12.2 | 16.8 | 16.7 | 15.4 | 14.6 | 15.1 |
| | IV-6 | 41 | 19.9 | 10.7 | 14.6 | 15.4 | 12.0 | 11.4 | 12.1 | 14.4 | 12.5 | 9.8 | 11.2 | 12.4 |
| | IV-7 | 41 | 46.6 | 33.2 | 38.5 | 34.2 | 42.7 | 35.9 | 30.0 | 37.2 | 36.8 | 30.2 | 34.4 | 35.3 |
| | IV-8 | 40 | 30.4 | 27.2 | 21.4 | 20.0 | 19.4 | 22.1 | 25.6 | 25.6 | 25.1 | 20.1 | 22.1 | 22.9 |
| | IV-9 | 42 | 18.4 | 10.2 | 16.5 | 14.9 | 10.2 | 10.0 | 11.1 | 8.4 | 16.5 | 9.2 | 10.0 | 11.7 |
| | IV-10 | 41 | 18.0 | 7.2 | 7.6 | 6.6 | 9.2 | 12.5 | 9.9 | 12.4 | 11.2 | 13.2 | 10.0 | 10.0 |
| | IV-11 | 41 | 21.2 | 14.4 | 19.8 | 11.2 | 14.0 | 12.1 | 19.6 | 11.2 | 10.0 | 19.9 | 10.1 | 14.2 |
| | IV-12 | 41 | 24.2 | 17.4 | 16.6 | 14.1 | 19.2 | 18.0 | 12.6 | 14.5 | 19.2 | 13.5 | 18.4 | 16.4 |
| | IV-13 | 42 | 50.8 | 40.0 | 39.2 | 40.3 | 41.7 | 42.4 | 40.6 | 43.2 | 40.0 | 41.2 | 41.4 | 41.0 |
| | IV-14 | 40 | 40.7 | 30.6 | 30.2 | 31.4 | 34.2 | 35.6 | 32.4 | 30.1 | 31.2 | 33.2 | 30.7 | 32.0 |
| | IV-15 | 41 | 34.1 | 23.6 | 27.2 | 26.4 | 26.6 | 26.6 | 29.2 | 26.7 | 25.1 | 20.6 | 22.1 | 25.4 |
| | IV-16 | 41 | 55.2 | 46.1 | 50.0 | 44.2 | 41.1 | 40.2 | 39.4 | 45.1 | 40.2 | 40.8 | 41.3 | 42.8 |
| | IV-17 | 40 | 32.4 | 23.6 | 21.2 | 26.6 | 24.5 | 22.2 | 24.1 | 20.4 | 20.0 | 25.7 | 21.4 | 23.0 |
| | IV-18 | 42 | 26.2 | 20.4 | 19.2 | 21.2 | 20.6 | 19.4 | 17.2 | 18.6 | 19.9 | 21.1 | 21.4 | 19.9 |
| | IV-19 | 41 | 30.7 | 20.2 | 24.6 | 23.8 | 24.6 | 24.4 | 20.6 | 23.8 | 23.1 | 22.2 | 24.2 | 23.2 |
| | IV-20 | 40 | 29.5 | 22.1 | 27.2 | 20.6 | 21.7 | 20.9 | 23.4 | 24.1 | 21.2 | 20.6 | 20.9 | 22.3 |
| | IV-21 | 41 | 26.4 | 21.4 | 17.0 | 19.6 | 20.0 | 19.4 | 22.1 | 21.4 | 20.6 | 20.2 | 22.2 | 20.4 |
| | IV-22 | 41 | 41.6 | 35.4 | 36.2 | 32.1 | 28.6 | 31.4 | 30.0 | 26.2 | 25.8 | 29.2 | 34.4 | 30.9 |
| | IV-23 | 40 | 24.1 | 19.2 | 18.6 | 16.9 | 15.4 | 14.6 | 12.5 | 16.4 | 17.2 | 8.2 | 16.6 | 15.6 |
| Example | IV-24 | 42 | 29.3 | 21.2 | 20.2 | 19.2 | 24.1 | 22.6 | 23.5 | 24.4 | 20.6 | 18.6 | 19.9 | 21.4 |
| | IV-25 | 41 | 32.6 | 26.4 | 19.2 | 26.6 | 23.5 | 24.3 | 19.4 | 20.9 | 22.2 | 25.2 | 20.6 | 22.8 |
| | IV-26 | 40 | 59.8 | 45.8 | 51.2 | 46.6 | 42.5 | 45.3 | 40.6 | 41.3 | 50.0 | 48.2 | 44.9 | 45.6 |
| | IV-27 | 42 | 50.1 | 40.2 | 41.1 | 42.3 | 39.6 | 44.5 | 38.2 | 36.9 | 42.1 | 35.1 | 44.6 | 40.5 |
| | IV-28 | 40 | 53.7 | 50.2 | 42.2 | 36.9 | 42.0 | 37.6 | 40.2 | 44.6 | 42.3 | 41.2 | 35.2 | 41.2 |
| | IV-29 | 42 | 53.2 | 42.1 | 36.6 | 42.2 | 37.2 | 38.6 | 40.2 | 40.7 | 44.4 | 42.6 | 42.5 | 40.7 |
| | IV-30 | 41 | 41.1 | 30.2 | 26.6 | 33.1 | 32.1 | 29.4 | 31.1 | 30.0 | 28.5 | 31.4 | 31.9 | 30.4 |
| | IV-31 | 40 | 60.2 | 46.3 | 50.6 | 49.2 | 41.2 | 43.3 | 42.1 | 50.6 | 44.0 | 40.4 | 49.5 | 45.7 |
| | IV-32 | 41 | 40.6 | 30.6 | 31.2 | 34.2 | 35.2 | 36.1 | 38.2 | 30.9 | 30.0 | 31.4 | 32.4 | 33.0 |
| | IV-33 | 40 | 45.3 | 37.2 | 39.4 | 36.2 | 35.3 | 33.9 | 32.4 | 35.6 | 30.2 | 39.4 | 36.6 | 35.6 |
| | IV-34 | 40 | 57.9 | 44.2 | 42.9 | 46.5 | 44.9 | 44.2 | 44.3 | 46.2 | 51.2 | 42.1 | 44.9 | 45.1 |
| | IV-35 | 41 | 72.4 | 60.2 | 69.2 | 65.4 | 66.2 | 68.2 | 66.3 | 69.4 | 65.2 | 60.0 | 59.4 | 65.0 |
| | IV-36 | 40 | 60.9 | 49.2 | 48.4 | 50.6 | 49.2 | 50.6 | 49.6 | 46.8 | 45.7 | 43.9 | 42.0 | 47.6 |
| | IV-37 | 40 | 64.1 | 50.2 | 51.4 | 50.2 | 51.2 | 50.3 | 44.2 | 46.2 | 45.9 | 53.4 | 52.7 | 49.6 |
| | IV-38 | 42 | 52.4 | 40.2 | 44.2 | 40.6 | 39.3 | 35.3 | 38.6 | 43.2 | 39.9 | 40.2 | 44.0 | 40.6 |
| | IV-39 | 41 | 40.6 | 30.2 | 35.3 | 33.4 | 32.6 | 37.2 | 34.5 | 34.2 | 35.6 | 29.2 | 34.2 | 33.6 |
| | IV-40 | 40 | 58.3 | 40.2 | 46.4 | 46.2 | 48.3 | 49.2 | 41.1 | 42.6 | 48.4 | 43.2 | 46.7 | 45.2 |
| | IV-41 | 41 | 39.9 | 30.6 | 28.2 | 34.4 | 35.2 | 36.2 | 32.1 | 30.6 | 31.2 | 30.0 | 33.8 | 32.2 |
| | IV-42 | 42 | 44.1 | 36.2 | 40.0 | 41.2 | 34.2 | 35.8 | 36.2 | 37.2 | 28.9 | 29.4 | 31.2 | 35.0 |
| | IV-43 | 41 | 56.0 | 49.2 | 51.2 | 46.2 | 44.4 | 43.2 | 45.2 | 46.6 | 42.1 | 49.3 | 51.4 | 46.9 |
| | IV-44 | 40 | 70.2 | 60.2 | 66.3 | 65.4 | 66.1 | 62.3 | 64.2 | 60.8 | 61.2 | 63.4 | 65.5 | 63.5 |
| | IV-45 | 41 | 57.5 | 50.2 | 41.1 | 48.6 | 49.2 | 44.7 | 49.2 | 46.2 | 39.4 | 42.1 | 44.6 | 45.5 |
| | IV-46 | 40 | 61.7 | 50.5 | 50.2 | 51.3 | 52.4 | 53.6 | 52.4 | 50.9 | 51.4 | 48.6 | 46.3 | 50.8 |
| Example | IV-47 | 37 | 14.6 | 9.2 | 7.6 | 11.2 | 7.1 | 8.9 | 9.6 | 8.5 | 7.4 | 9.9 | 11.1 | 9.1 |
| | IV-48 | 35 | 14.9 | 10.2 | 10.2 | 6.1 | 8.8 | 7.5 | 10.2 | 4.9 | 11.4 | 12.2 | 11.6 | 9.3 |
| | IV-49 | 36 | 25.3 | 12.1 | 19.6 | 18.8 | 18.6 | 19.4 | 14.6 | 17.2 | 18.5 | 16.6 | 16.4 | 17.2 |
| | IV-50 | 36 | 13.7 | 9.2 | 8.5 | 6.3 | 8.8 | 10.0 | 9.2 | 8.6 | 6.4 | 4.2 | 8.3 | 8.0 |
| | IV-51 | 35 | 18.6 | 12.2 | 6.2 | 13.2 | 12.1 | 12.1 | 13.6 | 9.1 | 8.2 | 8.6 | 10.2 | 10.6 |
| | IV-52 | 36 | 20.1 | 10.6 | 16.4 | 15.2 | 15.2 | 15.2 | 13.8 | 11.4 | 16.2 | 9.5 | 14.2 | 13.8 |
| | IV-53 | 35 | 45.0 | 36.4 | 32.5 | 33.5 | 40.0 | 36.2 | 39.4 | 35.2 | 30.6 | 33.1 | 41.2 | 35.8 |
| | IV-54 | 37 | 36.3 | 30.0 | 29.5 | 31.2 | 30.5 | 29.3 | 30.6 | 30.6 | 31.4 | 32.4 | 28.7 | 30.4 |
| | IV-55 | 35 | 30.2 | 18.9 | 24.2 | 23.6 | 25.2 | 20.2 | 21.9 | 24.2 | 20.0 | 19.9 | 24.6 | 22.3 |
| | IV-56 | 29 | 7.2 | 4.6 | 3.0 | 4.9 | 5.2 | 6.3 | 5.8 | 4.9 | 3.6 | 4.2 | 4.1 | 4.7 |
| | IV-57 | 31 | 16.6 | 12.1 | 10.6 | 10.2 | 9.2 | 14.2 | 13.6 | 12.4 | 10.4 | 8.8 | 8.9 | 11.0 |

TABLE IV-2-continued

| Example No. | Water absorption capacity (g/g polymer) | Gel strength <Urine of human adult> (g/cm²) | Stability of gel <Urine of human adult> (g/cm²) | | | | | | | | | | |
|---|---|---|---|---|---|---|---|---|---|---|---|---|---|
| | | | RUN 1 | RUN 2 | RUN 3 | RUN 4 | RUN 5 | RUN 6 | RUN 7 | RUN 8 | RUN 9 | RUN 10 | Average |
| IV-58 | 35 | 17.0 | 9.1 | 12.3 | 10.6 | 9.4 | 12.1 | 13.1 | 14.2 | 8.3 | 12.1 | 7.6 | 10.9 |
| IV-59 | 36 | 15.2 | 9.0 | 7.2 | 12.1 | 10.2 | 12.1 | 13.1 | 12.6 | 8.4 | 6.2 | 12.6 | 10.4 |
| IV-60 | 36 | 16.1 | 12.1 | 11.1 | 10.9 | 12.1 | 13.3 | 12.6 | 13.4 | 13.5 | 14.2 | 16.6 | 13.0 |
| IV-61 | 40 | 60.4 | 50.2 | 51.4 | 49.6 | 45.3 | 52.1 | 46.5 | 53.1 | 54.2 | 45.5 | 45.6 | 49.4 |
| IV-62 | 41 | 74.5 | 70.2 | 69.2 | 71.1 | 70.6 | 59.9 | 64.1 | 60.3 | 62.1 | 65.1 | 64.3 | 65.7 |
| IV-63 | 41 | 34.5 | 30.0 | 29.5 | 28.6 | 29.4 | 26.0 | 22.5 | 28.6 | 29.2 | 23.6 | 24.2 | 27.2 |
| IV-64 | 40 | 41.9 | 30.6 | 30.2 | 34.1 | 28.9 | 29.9 | 34.2 | 25.6 | 31.2 | 36.2 | 28.2 | 30.9 |
| IV-65 | 41 | 17.4 | 9.9 | 12.1 | 14.1 | 8.6 | 7.2 | 9.6 | 10.0 | 12.1 | 11.2 | 12.3 | 10.7 |
| IV-66 | 41 | 18.6 | 14.5 | 15.4 | 10.2 | 11.2 | 12.2 | 13.2 | 12.9 | 9.9 | 12.7 | 13.6 | 12.6 |
| IV-67 | 42 | 24.2 | 17.6 | 17.2 | 15.1 | 19.1 | 13.6 | 15.2 | 14.4 | 19.6 | 19.7 | 18.6 | 17.0 |
| IV-68 | 41 | 25.9 | 19.4 | 17.1 | 19.2 | 14.4 | 19.8 | 13.6 | 15.8 | 20.7 | 18.4 | 15.6 | 17.4 |

TABLE IV-3

| | Example No. | "Stickiness" on gel surface <Urine of human adult> | | | | | | | | | |
|---|---|---|---|---|---|---|---|---|---|---|---|
| | | RUN 1 | RUN 2 | RUN 3 | RUN 4 | RUN 5 | RUN 6 | RUN 7 | RUN 8 | RUN 9 | RUN 10 |
| Example | IV-1 | ○ | ○ | ○ | ○ | ○ | ○ | ○ | ○ | ○ | ○ |
| | IV-2 | ○ | ○ | Δ~○ | ○ | ○ | ○ | Δ~○ | ○ | ○ | ○ |
| | IV-3 | Δ~○ | Δ~○ | Δ~○ | Δ~○ | Δ~○ | Δ~○ | Δ~○ | ○ | ○ | Δ~○ |
| | IV-4 | ○ | Δ~○ | ○ | Δ~○ | ○ | Δ~○ | ○ | ○ | ○ | ○ |
| | IV-5 | ○ | ○ | Δ~○ | Δ~○ | ○ | Δ~○ | ○ | ○ | ○ | Δ~○ |
| | IV-6 | Δ~○ | Δ~○ | ○ | Δ~○ | Δ~○ | Δ~○ | Δ~○ | Δ~○ | Δ~○ | Δ~○ |
| | IV-7 | ○ | ○ | ○ | ○ | ○ | ○ | ○ | ○ | ○ | ○ |
| | IV-8 | ○ | ○ | ○ | ○ | ○ | ○ | ○ | ○ | ○ | ○ |
| | IV-9 | Δ~○ | ○ | Δ~○ | Δ~○ | Δ~○ | Δ~○ | Δ~○ | ○ | Δ~○ | Δ~○ |
| | IV-10 | Δ~○ | Δ~○ | Δ | Δ~○ | Δ~○ | Δ~○ | Δ~○ | Δ~○ | Δ~○ | Δ~○ |
| | IV-11 | Δ~○ | ○ | Δ~○ | Δ~○ | Δ~○ | ○ | Δ~○ | Δ~○ | ○ | Δ~○ |
| | IV-12 | ○ | ○ | Δ~○ | ○ | ○ | Δ~○ | Δ~○ | ○ | Δ~○ | ○ |
| | IV-13 | ○ | ○ | ○ | ○ | ○ | ○ | ○ | ○ | ○ | ○ |
| | IV-14 | ○ | ○ | ○ | ○ | ○ | ○ | ○ | ○ | ○ | ○ |
| | IV-15 | ○ | ○ | ○ | ○ | ○ | ○ | ○ | ○ | ○ | ○ |
| | IV-16 | ○ | ○ | ○ | ○ | ○ | ○ | ○ | ○ | ○ | ○ |
| | IV-17 | ○ | ○ | ○ | ○ | ○ | ○ | ○ | ○ | ○ | ○ |
| | IV-18 | ○ | ○ | ○ | ○ | ○ | ○ | ○ | ○ | ○ | ○ |
| | IV-19 | ○ | ○ | ○ | ○ | ○ | ○ | ○ | ○ | ○ | ○ |
| | IV-20 | ○ | ○ | ○ | ○ | ○ | ○ | ○ | ○ | ○ | ○ |
| | IV-21 | ○ | ○ | ○ | ○ | ○ | ○ | ○ | ○ | ○ | ○ |
| | IV-22 | ○ | ○ | ○ | ○ | ○ | ○ | ○ | ○ | ○ | ○ |
| | IV-23 | ○ | ○ | ○ | ○ | Δ~○ | Δ~○ | ○ | ○ | Δ | ○ |
| Example | IV-24 | ○ | ○ | ○ | ○ | ○ | ○ | ○ | ○ | ○ | ○ |
| | IV-25 | ○ | ○ | ○ | ○ | ○ | ○ | ○ | ○ | ○ | ○ |
| | IV-26 | ○ | ○ | ○ | ○ | ○ | ○ | ○ | ○ | ○ | ○ |
| | IV-27 | ○ | ○ | ○ | ○ | ○ | ○ | ○ | ○ | ○ | ○ |
| | IV-28 | ○ | ○ | ○ | ○ | ○ | ○ | ○ | ○ | ○ | ○ |
| | IV-29 | ○ | ○ | ○ | ○ | ○ | ○ | ○ | ○ | ○ | ○ |
| | IV-30 | ○ | ○ | ○ | ○ | ○ | ○ | ○ | ○ | ○ | ○ |
| | IV-31 | ○ | ○ | ○ | ○ | ○ | ○ | ○ | ○ | ○ | ○ |
| | IV-32 | ○ | ○ | ○ | ○ | ○ | ○ | ○ | ○ | ○ | ○ |
| | IV-33 | ○ | ○ | ○ | ○ | ○ | ○ | ○ | ○ | ○ | ○ |
| | IV-34 | ○ | ○ | ○ | ○ | ○ | ○ | ○ | ○ | ○ | ○ |
| | IV-35 | ○ | ○ | ○ | ○ | ○ | ○ | ○ | ○ | ○ | ○ |
| | IV-36 | ○ | ○ | ○ | ○ | ○ | ○ | ○ | ○ | ○ | ○ |
| | IV-37 | ○ | ○ | ○ | ○ | ○ | ○ | ○ | ○ | ○ | ○ |
| | IV-38 | ○ | ○ | ○ | ○ | ○ | ○ | ○ | ○ | ○ | ○ |
| | IV-39 | ○ | ○ | ○ | ○ | ○ | ○ | ○ | ○ | ○ | ○ |
| | IV-40 | ○ | ○ | ○ | ○ | ○ | ○ | ○ | ○ | ○ | ○ |
| | IV-41 | ○ | ○ | ○ | ○ | ○ | ○ | ○ | ○ | ○ | ○ |
| | IV-42 | ○ | ○ | ○ | ○ | ○ | ○ | ○ | ○ | ○ | ○ |
| | IV-43 | ○ | ○ | ○ | ○ | ○ | ○ | ○ | ○ | ○ | ○ |
| | IV-44 | ○ | ○ | ○ | ○ | ○ | ○ | ○ | ○ | ○ | ○ |
| | IV-45 | ○ | ○ | ○ | ○ | ○ | ○ | ○ | ○ | ○ | ○ |
| | IV-46 | ○ | ○ | ○ | ○ | ○ | ○ | ○ | ○ | ○ | ○ |
| Example | IV-47 | Δ | Δ | Δ~○ | Δ~○ | Δ | Δ | Δ | Δ~○ | Δ~○ | Δ~○ |
| | IV-48 | Δ~○ | Δ~○ | Δ | Δ~○ | Δ~○ | Δ~○ | Δ | Δ~○ | Δ~○ | Δ~○ |
| | IV-49 | Δ~○ | ○ | ○ | ○ | ○ | Δ~○ | Δ~○ | ○ | ○ | ○ |
| | IV-50 | Δ~○ | Δ~○ | Δ | Δ~○ | Δ~○ | Δ~○ | Δ~○ | Δ | Δ | Δ~○ |
| | IV-51 | Δ~○ | Δ | Δ~○ | Δ~○ | Δ~○ | Δ~○ | Δ~○ | Δ~○ | Δ~○ | Δ~○ |
| | IV-52 | Δ~○ | ○ | ○ | ○ | ○ | Δ~○ | Δ~○ | ○ | Δ~○ | Δ~○ |

TABLE IV-3-continued

"Stickiness" on gel surface <Urine of human adult>

| Example No. | RUN 1 | RUN 2 | RUN 3 | RUN 4 | RUN 5 | RUN 6 | RUN 7 | RUN 8 | RUN 9 | RUN 10 |
|---|---|---|---|---|---|---|---|---|---|---|
| IV-53 | ○ | ○ | ○ | ○ | ○ | ○ | ○ | ○ | ○ | ○ |
| IV-54 | ○ | ○ | ○ | ○ | ○ | ○ | ○ | ○ | ○ | ○ |
| IV-55 | ○ | ○ | ○ | ○ | ○ | ○ | ○ | ○ | ○ | ○ |
| IV-56 | Δ | Δ~X | Δ | Δ | Δ | Δ | Δ | Δ~X | Δ | Δ |
| IV-57 | Δ~○ | Δ~○ | Δ~○ | Δ~○ | Δ~○ | Δ~○ | Δ~○ | Δ~○ | Δ~○ | Δ~○ |
| IV-58 | Δ~○ | Δ~○ | Δ~○ | Δ~○ | Δ~○ | Δ~○ | Δ~○ | Δ~○ | Δ~○ | Δ~○ |
| IV-59 | Δ~○ | Δ~○ | Δ~○ | Δ~○ | Δ~○ | Δ~○ | Δ~○ | Δ~○ | Δ | Δ~○ |
| IV-60 | Δ~○ | Δ~○ | Δ~○ | Δ~○ | Δ~○ | Δ~○ | Δ~○ | Δ~○ | Δ~○ | ○ |
| IV-61 | ○ | ○ | ○ | ○ | ○ | ○ | ○ | ○ | ○ | ○ |
| IV-62 | ○ | ○ | ○ | ○ | ○ | ○ | ○ | ○ | ○ | ○ |
| IV-63 | ○ | ○ | ○ | ○ | ○ | ○ | ○ | ○ | ○ | ○ |
| IV-64 | ○ | ○ | ○ | ○ | ○ | ○ | ○ | ○ | ○ | ○ |
| IV-65 | Δ~○ | Δ~○ | Δ~○ | Δ~○ | Δ~○ | Δ~○ | Δ~○ | Δ~○ | Δ~○ | Δ~○ |
| IV-66 | Δ~○ | ○ | Δ~○ | Δ~○ | Δ~○ | Δ~○ | Δ~○ | Δ~○ | Δ~○ | Δ~○ |
| IV-67 | ○ | ○ | ○ | ○ | Δ~○ | ○ | Δ~○ | ○ | ○ | ○ |
| IV-68 | ○ | ○ | ○ | Δ~○ | ○ | Δ~○ | ○ | ○ | ○ | ○ |

EXAMPLE V-1

9 g of water was added to a slurry consisting of 100 g of the highly water-absorptive polymer (A) and 100 g of cyclohexane with stirring. To this mixture was added 1 g of di-n-butoxybis(triethanolaminat)titanium at a temperature of 50° C., followed by mixing for 30 minutes. Subsequently, the resulting mixture was dried at a bath temperature of 105° C. under reduced pressure for 30 minutes to obtain a highly water-absorptive polymer.

EXAMPLE V-2

10 g of water was added to a slurry consisting of 100 g of the highly water-absorptive polymer (A) and 100 g of cyclohexane with stirring. To this mixture was added 2 g of di-i-propoxybis(acetylacetonat)titanium at a temperature of 10° C., followed by mixing for 30 minutes. Subsequently, the resulting mixture was dried at a bath temperature of 105° C. under reduced pressure for 30 minutes to obtain a highly water-absorptive polymer.

EXAMPLE V-3

6 g of water was added to a slurry consisting of 100 g of the highly water-absorptive polymer (A) and 100 g of cyclohexane with stirring. To this mixture was added 0.2 g of tetraisopropoxytitanium at a temperature of 10° C., followed by mixing for 30 minutes. Subsequently, the resulting mixture was dried at a bath temperature of 105° C. under reduced pressure for 30 minutes to obtain a highly water-absorptive polymer.

EXAMPLE V-4

6g of water was added to a slurry consisting of 100 g of the highly water-absorptive polymer (A) and 100 g of cyclohexane with stirring. To this mixture was added 0.5 g of tetraisopropoxytitanium at a temperature of 10° C., followed by mixing for 30 minutes. Subsequently, the resulting mixture was dried at a bath temperature of 105° C. under reduced pressure for 30 minutes to obtain a highly water-absorptive polymer.

EXAMPLE V-5

0.5 g of tetraisopropoxytitanium was added to a slurry consisting of 100 g of the highly water-absorptive polymer (A) and 100 g of cyclohexane at a temperature of 10° C. with stirring, followed by mixing for 30 minutes. Subsequently, the resulting mixture was dried at a bath temperature of 105° C. under reduced pressure for 30 minutes to obtain a highly water-absorptive polymer.

EXAMPLE V-6

6 g of water was added to a slurry consisting of 100 g of the highly water-absorptive polymer (A) and 100 g of cyclohexane with stirring. To this mixture was added 1.0 g of tetraisopropoxytitanium at a temperature of 10° C., followed by mixing for 30 minutes. Subsequently, the resulting mixture was dried at a bath temperature of 105° C. under reduced pressure for 30 minutes to obtain a highly water-absorptive polymer.

EXAMPLE V-7

1.0 g of tetraisopropoxytitanium was added to a slurry consisting of 100 g of the highly water-absorptive polymer (A) and 100 g of cyclohexane at a temperature of 10° C. with stirring, followed by mixing for 30 minutes. Subsequently, the resulting mixture was dried at a bath temperature of 105° C. under reduced pressure for 30 minutes to obtain a highly water-absorptive polymer.

EXAMPLE V-8

25 g of water was added to a slurry consisting of 100 g of the highly water-absorptive polymer (A) and 100 g of cyclohexane with stirring. To this mixture was added 1 g of a tetra-n-butoxytitanium polymer ("B-4" manufactured by Nippon Soda Co., Ltd.) at a temperature of 50° C., followed by mixing for 30 minutes. Subsequently, the resulting mixture was dried at a bath temperature of 105° C. under reduced pressure for 30 minutes to obtain a highly water-absorptive polymer.

EXAMPLE V-9

20 g of water was added to a slurry consisting of 100 g of the highly water-absorptive polymer (A) and 100 g of cyclohexane with stirring. To this mixture was added 3 g of tetrastearyloxytitanium at a temperature of 50° C., followed by mixing for 30 minutes. Subsequently, the resulting mixture was dried at a bath temperature of 105° C. under reduced pressure for 30 minutes to obtain a highly water-absorptive polymer.

EXAMPLE V-10

9 g of water was added to a slurry consisting of 100 g of the highly water-absorptive polymer (B) and 100 g of cyclohexane with stirring. To this mixture was added 1 g of di-n-butoxybis(triethanolaminat)titanium at a temperature of 50° C., followed by mixing for 30 minutes. Subsequently, the resulting mixture was dried at a bath temperature of 105° C. under reduced pressure for 30 minutes to obtain a highly water-absorptive polymer.

EXAMPLE V-11

6 g of water was added to a slurry consisting of 100 g of the highly water-absorptive polymer (B) and 100 g of cyclohexane with stirring. To this mixture was added 0.5 g of tetraisopropoxytitanium at a temperature of 10° C., followed by mixing for 30 minutes. Subsequently, the resulting mixture was dried at a bath temperature of 105° C. under reduced pressure for 30 minutes to obtain a highly water-absorptive polymer.

EXAMPLE V-12

0.5 g of tetraisopropoxytitanium was added to a slurry consisting of 100 g of the highly water-absorptive polymer (B) and 100 g of cyclohexane at a temperature of 10° C. with stirring, followed by mixing for 30 minutes. Subsequently, the resulting mixture was dried at a bath temperature of 105° C. under reduced pressure for 30 minutes to obtain a highly water-absorptive polymer.

EXAMPLE V-13

20 g of water was added to a slurry consisting of 100 g of the highly water-absorptive polymer (B) and 100 g of cyclohexane with stirring. To this mixture was added 3 g of tetrastearyloxytitanium at a temperature of 50° C., followed by mixing for 30 minutes. Subsequently, the resulting mixture was dried at a bath temperature of 105° C. under reduced pressure for 30 minutes to obtain a highly water-absorptive polymer.

EXAMPLE V-14

9 g of water was added to a slurry consisting of 100 g of the highly water-absorptive polymer (C) and 100 g of cyclohexane with stirring. To this mixture was added 1 g of di-n-butoxybis(triethanolaminat)titanium at a temperature of 50° C., followed by mixing for 30 minutes. Subsequently, the resulting mixture was dried at a bath temperature of 105° C. under reduced pressure for 30 minutes to obtain a highly water-absorptive polymer.

EXAMPLE V-15

6 g of water was added to a slurry consisting of 100 g of the highly water-absorptive polymer (C) and 100 g of cyclohexane with stirring. To this mixture was added 0.5 g of tetraisopropoxytitanium at a temperature of 10° C., followed by mixing for 30 minutes. Subsequently, the resulting mixture was dried at a bath temperature of 105° C. under reduced pressure for 30 minutes to obtain a highly water-absorptive polymer.

EXAMPLE V-16

6 g of water was added to a slurry consisting of 100 g of the highly water-absorptive polymer (D) and 100 g of cyclohexane with stirring. To this mixture was added 0.5 g of tetraisopropoxytitanium at a temperature of 10° C., followed by mixing for 30 minutes. Subsequently, the resulting mixture was dried at a bath temperature of 105° C. under reduced pressure for 30 minutes to obtain a highly water-absorptive polymer.

The highly water-absorptive polymers obtained were subjected to the above-described measurements. The results are shown in Table V-1.

COMPARATIVE EXAMPLES V-1 TO V-4

The highly water-absorptive polymers (A), (B), (C) and (D) (Comparative Examples V-1, V-2, V-3 and V-4, respectively), which were not subjected to the alkoxytitanium treatment according to the present invention, were subjected to the above-described measurements. The results are shown in Table V-1.

TABLE V-1

| Example No. | | Water absorption capacity (g/g polymer) | Gel strength <Urine of human adult> (g/cm$^2$) | Stability of gel <Urine of human adult> (g/cm$^2$) | | | | | "Stickiness" on gel surface <Urine of human adult> | | | | |
|---|---|---|---|---|---|---|---|---|---|---|---|---|---|
| | | | | RUN 1 | RUN 2 | RUN 3 | RUN 4 | RUN 5 | RUN 1 | RUN 2 | RUN 3 | RUN 4 | RUN 5 |
| Example | V-1 | 40 | 32.6 | 28.8 | 29.4 | 30.0 | 25.8 | 28.0 | Δ~○ | Δ~○ | ○ | Δ | Δ~○ |
| | V-2 | 41 | 29.9 | 27.2 | 28.8 | 25.4 | 27.2 | 29.0 | ○ | Δ~○ | Δ | ○ | ○ |
| | V-3 | 41 | 48.2 | 35.2 | 34.6 | 38.9 | 35.2 | 36.5 | ○ | Δ~○ | ○ | ○ | ○ |
| | V-4 | 40 | 57.1 | 45.2 | 48.8 | 47.9 | 49.2 | 48.7 | ○ | ○ | ○ | ○ | ○ |
| | V-5 | 41 | 32.9 | 28.8 | 29.5 | 27.7 | 28.8 | 24.4 | ○ | ○ | Δ~○ | ○ | Δ~○ |
| | V-6 | 39 | 82.4 | 58.6 | 55.9 | 54.6 | 59.3 | 58.8 | ○ | ○ | ○ | ○ | ○ |
| | V-7 | 41 | 38.6 | 30.6 | 31.2 | 28.8 | 34.2 | 37.1 | ○ | ○ | Δ~○ | ○ | ○ |
| | V-8 | 42 | 30.0 | 27.2 | 25.6 | 28.4 | 29.0 | 24.2 | Δ~○ | Δ | Δ~○ | ○ | Δ |
| | V-9 | 41 | 29.4 | 27.2 | 25.3 | 25.3 | 26.2 | 28.4 | Δ~○ | Δ | Δ | Δ~○ | Δ~○ |
| | V-10 | 36 | 25.0 | 20.0 | 24.0 | 20.8 | 20.9 | 21.2 | Δ~○ | ○ | Δ~○ | Δ~○ | Δ~○ |
| | V-11 | 34 | 33.1 | 30.0 | 29.4 | 30.2 | 28.4 | 28.5 | ○ | Δ~○ | ○ | Δ~○ | Δ~○ |
| | V-12 | 35 | 20.4 | 16.6 | 17.0 | 14.9 | 21.1 | 15.3 | Δ~○ | Δ~○ | Δ | ○ | Δ |
| | V-13 | 35 | 28.2 | 24.2 | 22.5 | 20.8 | 22.8 | 26.0 | Δ~○ | Δ~○ | Δ~○ | Δ~○ | ○ |
| | V-14 | 28 | 10.5 | 9.5 | 8.2 | 8.6 | 7.5 | 8.0 | Δ | Δ~X | Δ~X | Δ | Δ~X |
| | V-15 | 30 | 11.0 | 7.2 | 8.6 | 9.0 | 8.2 | 7.5 | Δ~X | Δ~X | Δ | Δ | Δ~X |
| | V-16 | 35 | 27.4 | 21.2 | 22.1 | 23.2 | 20.6 | 21.2 | Δ | Δ~○ | Δ~○ | Δ | Δ~○ |
| Comp. Ex. | V-1 | 41 | 14.7 | —* | — | — | — | 3.5 | X | X | X | X | X |
| | V-2 | 35 | 18.2 | — | 0.6 | — | — | — | X | X | X | X | X |
| | V-3 | 30 | 5.0 | — | — | — | — | — | X | X | X | X | X |
| | V-4 | 36 | 14.0 | — | 5.4 | — | — | 0.2 | X | Δ~X | X | X | X |

*In the table, "—" means that the measurement was not able to be carried out because the swollen gel was in a semifluid state.

What is claimed is:

1. A highly water-absorptive polymer composition comprising a mixture of the following components (A) and (B):
   (A) 100 parts by weight of a highly water-absorptive polymer having a crosslinked structure, comprising as its constituent a carboxyl group and/or a carboxylate group; and
   (B) 0.05 to 10 parts by weight of an additive selected from the group consisting of oxalic acid and salts, amides, esters, nitrites, and hydrazides of oxalic acid; a sulfate of a metal selected from the group consisting of titanium, zirconium and vanadium; and a crystalline or noncrystalline, high-purity particulate titania having a mean particle diameter of 1 μm or less, a specific surface area of 10 m$^2$/g or more as determined by the Brunauer-Emmett-Teller method, and, when crystalline, a crystal structure of a mixed typed of rutile and anatase,
   said mixture being prepared by mechanically dry blending the components (A) and (B).

2. The highly water-absorptive polymer composition according to claim 1, wherein the additive is oxalic acid or a oxalic acid salt selected from the group consisting of potassium oxalate, sodium oxalate, potassium oxalate titanate, sodium oxalate titanate and ammonium oxalate titanate.

3. The highly water-absorptive polymer composition according to claim 1, wherein the additive is an oxalic acid salt, and the highly water-absorptive polymer composition further comprises a polyvalent metal compound, the total amount of the oxalic acid salt and the polyvalent metal compound being from 0.05 to 10 parts by weight per 100 parts by weight of the highly water-absorptive polymer, and the blend ratio (weight basis) of the oxalic acid salt to the polyvalent metal compound being from 90:10 to 10:90.

4. The highly water-absorptive polymer composition according to claim 3, wherein the polyvalent metal compound is a metal oxide or metal sulfate wherein the metal is selected from the group consisting of silicon, titanium, zirconium and vanadium.

5. The highly water-absorptive polymer composition according to claim 1, wherein the additive is a sulfate of a metal selected from the group consisting of titanium sulfate, titanyl sulfate, zirconium sulfate and vanadyl sulfate.

6. The highly water-absorptive polymer composition according to claim 1, wherein the additive is the high-purity particulate titania having a specific surface area of 30 m$^2$/g or more.

7. The highly water-absorptive polymer composition according to claim 1, wherein the highly water-absorptive polymer is selected from the group consisting of a crosslinked polyacrylic acid salt, a crosslinked graft copolymer of starch and an acrylic acid salt, a hydrolyzate of a crosslinked starch-acrylonitrile graft copolymer, a hydrolyzate of a crosslinked acrylate-vinyl acetate copolymer, a crosslinked copolymer of an acrylic acid salt and acrylamide, and a hydrolyzate of a crosslinked polyacrylonitrile.

8. The highly water-absorptive polymer composition according to claim 1, wherein the highly water-absorptive polymer is one which has undergone surface-crosslinking with a crosslinking agent having two or more functional groups reactive with the carboxyl group and/or the carboxylate group.

9. The highly water-absorptive polymer according to claim 8, wherein the crosslinking agent is a polydiglycidyl ether compound.

10. The highly water-absorptive polymer composition according to claim 1, wherein the highly water-absorptive polymer is one which has undergone surface modification with a silane compound represented by the following general formula:

$$X(R)_m Si(Y)_{3-m}$$

wherein X represents a functional group which can react with the carboxyl group and/or the carboxylate group in the highly water-absorptive polymer, R represents a hydrocarbon group, Y represents a hydrolyzable group, and m is 0, 1 or 2.

11. The highly water-absorptive polymer composition according to claim 10, wherein the silane compound is selected from the group consisting of γ-glycidoxypropyltrimethoxysilane,
γ-glycidoxypropylmethyldiethoxysilane,
β-(3,4-epoxycyclohexyl)ethyltrimethoxysilane,
γ-(2-aminoethyl)aminopropyltrimethoxysilane,
γ-(2-aminoethyl)aminopropylmethyldimethoxysilane,
γ-aminopropyltriethoxysilane,
N-phenyl-γ-aminopropyltrimethoxysilane,
γ-mercaptopropyltrimethoxysilane,
γ-mercaptopropylmethyldimethoxysilane,
γ-chloropropyltrimethoxysilane,
γ-chloropropylmethyldimethoxysilane and octadecyldimethyl[3-(trimethoxysilyl)propyl] ammonium chloride.

12. The highly water-absorptive polymer composition according to claim 7, wherein the additive is a sulfate of a metal selected from the group consisting of titanium sulfate, titanyl sulfate, zirconium sulfate and vanadyl sulfate.

13. The highly water-absorptive polymer composition according to claim 10, wherein the additive is a sulfate of a metal selected from the group consisting of titanium sulfate, titanyl sulfate, zirconium sulfate and vanadyl sulfate.

14. A method for producing a highly water-absorptive polymer having enhanced gel strength, which comprises contacting with an alkoxytitanium a highly water-absorptive polymer having a crosslinked structure, comprising as its constituent a carboxyl group and/or a carboxylate group.

15. The method according to claim 14, wherein the highly water-absorptive polymer is selected from the group consisting of a crosslinked polyacrylic acid salt, a crosslinked graft copolymer of starch and an acrylic acid salt, a hydrolyzate of a crosslinked starch-acrylonitrile graft copolymer, a hydrolyzate of a crosslinked acrylate-vinyl acetate copolymer, a crosslinked copolymer of an acrylic acid salt and acrylamide, and a hydrolyzate of a crosslinked polyacrylonitrile.

16. The method according to claim 14, wherein the highly water-absorptive polymer is one which has undergone surface-crosslinking with a crosslinking agent having two or more functional groups reactive with the carboxyl group and/or the carboxylate group.

17. The method according to claim 16, wherein the crosslinking agent is a polydiglycidyl ether compound.

18. The method according to claim 14, wherein the highly water-absorptive polymer is one which has undergone surface modification with a silane compound represented by the following general formula:

$$X(R)_m Si(Y)_{3-m}$$

wherein X represents a functional group which can react with the carboxyl group and/or the carboxylate group in the highly water-absorptive polymer, R represents a hydrocarbon group, Y represents a hydrolyzable group, and m is 0, 1 or 2.

19. The method according to claim 16, wherein the silane compound is selected from the group consisting of γ-glycidoxypropyltrimethoxysilane,
γ-glycidoxypropylmethyldiethoxysilane,
β-(3,4-epoxycyclohexyl)ethyltrimethoxysilane,
γ-(2-aminoethyl)aminopropyltrimethoxysilane,
γ-(2-aminoethyl)aminopropylmethyldimethoxysilane,
γ-aminopropyltriethoxysilane,
N-phenyl-γ-aminopropyltrimethoxysilane,
γ-mercaptopropyltrimethoxysilane,
γ-mercaptopropylmethyldimethoxysilane,
γ-chloropropyltrimethoxysilane,
γ-chloropropylmethyldimethoxysilane and octadecyldimethyl[3-(trimethoxysilyl)propyl] ammonium chloride.

\* \* \* \* \*